United States Patent
Larsen et al.

(10) Patent No.: US 10,293,094 B2
(45) Date of Patent: May 21, 2019

(54) SYSTEMS FOR UTILIZING THE WATER CONTENT IN FLUID FROM A RENAL REPLACEMENT THERAPY PROCESS

(71) Applicant: Aquaporin A/S, Kongens Lyngby (DK)

(72) Inventors: Marianne Eleonora Spanget Larsen, Store Heddinge (DK); Peter Holme Jensen, København Ø (DK); Michael Padkjær Abildgren, København Ø (DK)

(73) Assignee: Aquaporin A/S, Kongens Lyngby (DK)

( * ) Notice: Subject to any disclaimer, the term of this patent is extended or adjusted under 35 U.S.C. 154(b) by 241 days.

(21) Appl. No.: 15/121,179

(22) PCT Filed: Feb. 20, 2015

(86) PCT No.: PCT/EP2015/053598
§ 371 (c)(1),
(2) Date: Aug. 24, 2016

(87) PCT Pub. No.: WO2015/124716
PCT Pub. Date: Aug. 27, 2015

(65) Prior Publication Data
US 2017/0065762 A1   Mar. 9, 2017

(30) Foreign Application Priority Data

Jul. 17, 2014   (DK) .................. 2014 00398

(51) Int. Cl.
| | | |
|---|---|---|
| *A61M 1/34* | (2006.01) |
| *A61M 1/16* | (2006.01) |
| *B01D 61/00* | (2006.01) |
| *B01D 69/14* | (2006.01) |
| *B01D 61/14* | (2006.01) |
| *B01D 69/12* | (2006.01) |

(52) U.S. Cl.
CPC ........ *A61M 1/3479* (2014.02); *A61M 1/1696* (2013.01); *A61M 1/3431* (2014.02);
(Continued)

(58) Field of Classification Search
None
See application file for complete search history.

(56) References Cited

U.S. PATENT DOCUMENTS

| | | | |
|---|---|---|---|
| 2010/0121246 A1 | 5/2010 | Peters et al. | |
| 2012/0080377 A1* | 4/2012 | Jensen | B01D 11/0446 210/643 |

(Continued)

FOREIGN PATENT DOCUMENTS

| | | |
|---|---|---|
| DE | 19540079 A1 | 4/1997 |
| WO | WO-2009083011 A2 | 7/2009 |

(Continued)

OTHER PUBLICATIONS

Alsvik et al., "Pressure retarded osmosis and forward osmosis membranes: materials and methods," Polymers. 5(1):303-27 (2013).

(Continued)

*Primary Examiner* — Chester T Barry
(74) *Attorney, Agent, or Firm* — Clark & Elbing LLP

(57) ABSTRACT

The present invention relates to systems, methods and uses for recycling at least a part of water lost during various renal replacement therapy processes, e.g. in the preparation of a fresh dialysate solution or fresh reconstitution fluid for kidney disease dialysis and hemofiltration by utilizing water from the spent fluids. The system of the invention is useful in hemodialysis and in peritoneal dialysis as well as in hemofiltration for reuse of water from filtrates and spent fluids. In addition, the system of the invention is useful in the development of a renal assist device or artificial kidney.

26 Claims, 10 Drawing Sheets

(52) U.S. Cl.
CPC ........ *A61M 1/3434* (2014.02); *A61M 1/3437* (2014.02); *A61M 1/3458* (2014.02); *A61M 1/3468* (2014.02); *A61M 1/3472* (2013.01); *A61M 1/3482* (2014.02); *B01D 61/002* (2013.01); *B01D 61/145* (2013.01); *B01D 69/12* (2013.01); *B01D 69/144* (2013.01)

(56) References Cited

U.S. PATENT DOCUMENTS

| | | | |
|---|---|---|---|
| 2012/0080378 A1 | 4/2012 | Revanur et al. | |
| 2012/0152841 A1 | 6/2012 | Vissing et al. | |
| 2014/0255636 A1* | 9/2014 | Odeh | B01D 71/58 428/36.5 |
| 2015/0136690 A1* | 5/2015 | Xie | C02F 1/44 210/500.3 |

FOREIGN PATENT DOCUMENTS

| | | | | |
|---|---|---|---|---|
| WO | WO-2010/146365 A1 | 12/2010 | | |
| WO | WO-2012080946 A1 | 6/2012 | | |
| WO | WO-2012102678 A1 * | 8/2012 | ......... | B01D 67/0009 |
| WO | WO-2013/180659 A1 | 12/2013 | | |
| WO | WO-2014/075086 A1 | 5/2014 | | |
| WO | WO-2014128293 A1 | 8/2014 | | |
| WO | WO-2015124716 A1 | 8/2015 | | |

OTHER PUBLICATIONS

Brunkhorst et al., "Automated peritoneal dialysis with 'on-line'-prepared bicarbonate-buffered dialysate: technique and first clinical experiences," Nephrol Dial Transplant. 13(12):3189-92 (1998).

Discher et al., "Polymer vesicles in various media," Current Opinion in Colloid & Interface Science. 5(1-2):125-31 (2000).

Discher et al., "Polymer vesicles," Science. 297(5583):967-73 (2002).

Harris et al., "Spontaneous generation of multilamellar vesicles from ethylene oxide/butylene oxide diblock copolymers," Langmuir. 18(14):5337-42 (2002).

International Search Report and Written Opinion for International Application No. PCT/EP2015/053598, dated Jun. 5, 2015 (11 pages).

Issa et al., "Renal Assist Device and Treatment of Sepsis-Induced Acute kidney Injury in Intensive Care Units," *Contributions to Nephrology: Acute Kidney Injury*. Ronco, Bellomo, Kellum, vol. 156, 419-427 (2007). (12 pages).

Kumar et al., "Highly permeable polymeric membranes based on the incorporation of the functional water channel protein Aquaporin Z," PNAS, 2007, 104:52, 20719-20724.

Nardin et al., "Polymerized ABA triblock copolymer vesicles," Langmuir. 16(3):1035-41 (2000).

Ronco, "Recent evolution of renal replacement therapy in the critically ill patient," Crit Care. 10(1):123 (2006).

Sam et al., "Composition and clinical use of hemodialysates," Hemodial Int. 10(1):15-28 (2006).

Search Report for Danish Patent Application No. PA201400398, dated Sep. 29, 2014 (4 pages).

Sukitpaneenit et al., "High performance thin-film composite forward osmosis hollow fiber membranes with macrovoid-free and highly porous structure for sustainable water production," Environ Sci Technol. 46(13):7358-65 (2012).

Talaat, K.M., "Dialysis fluid regeneration by forward osmosis: A feasible option for ambulatory dialysis systems." Saudi J Kidney Dis Transpl 2010; 21(4): 748-749.

* cited by examiner

SYSTEMS FOR UTILIZING THE WATER CONTENT IN FLUID FROM A RENAL REPLACEMENT THERAPY PROCESS

FIELD OF THE INVENTION

The present invention relates to a system for recycling at least a part of water lost during various renal replacement therapy processes, e.g. in the preparation of a fresh dialysate solution or fresh replacement or reconstitution fluid for hemofiltration and kidney disease dialysis by utilizing water from the spent or waste fluids. Furthermore, the system of the invention is useful in a continuous renal replacement therapy, such as hemofiltration, as well as in hemodialysis and in peritoneal dialysis for reuse of water from filtrates and spent fluids. In addition, the system of the invention is useful in the development of a renal assist device or artificial kidney. Methods and uses of the systems and membranes of the present invention are also disclosed.

BACKGROUND OF THE INVENTION

Hemofiltration and dialysis, including hemodialysis and peritoneal dialysis, are different types of treatment for patients that suffer from kidney failure. In hemodialysis, the patient's blood is utilized to remove waste, toxins and excess water from the patient. The patient is connected to a hemodialysis machine and the patient's blood is pumped through the machine. Catheters are inserted into the patient's veins and arteries to connect the blood flow to and from the hemodialysis machine. As blood passes through a dialyzer in the hemodialysis machine, the dialyzer removes the waste, toxins and excess water from the patient's blood and returns the blood to infuse back into the patient. In hemofiltration, toxins and excess water are also removed from the patient's blood. However, in hemofiltration, the patient is connected to the hemofiltration system—intermittently or continuously—and blood from the patient passes through a system with a hemofilter. In contrast to hemodialysis, no dialysate is used in hemofiltration and the movement of solvent and solutes across the membrane is governed by convection rather than diffusion, mimicking the microfiltration process of a normal kidney. It may be necessary to add an isotonic replacement fluid to the blood—before or after the hemofilter—to replace losses of fluid volume and electrolytes. In continuous hemofiltration between 0 and 2000 mL of water may be lost per hour. This means that a considerable volume of water may have to be replaced depending on the individual patient's need. In hemofiltration, the demand for replacement fluid can be as much as 3 to 4 liters per hour.

In contrast, a large amount of dialysate, for example about 120 liters, is used to dialyze the blood during a single hemodialysis therapy. The spent dialysate in then discarded. This means that a patient undergoing hemodialysis therapy three times weekly could be exposed to nearly 600 liters of purified water. By comparison, a healthy individual would intake around 2 liters per day or 14 liters per week. In addition, large amounts of purified water are used for peritoneal dialysis, such as 12 liters per day during continuous ambulatory peritoneal dialysis, CAPD, and up to 25 liters per night during automatical fluid replacement while the patient is sleeping (automated peritoneal dialysis, APD). Dialysis is a life saving treatment for end stage kidney disease patients. However, it requires large scale consumption of highly purified water for the preparation of replacement fluids as well as dialysate solutions.

In WO2010/146365 A1 it has been suggested to recover purified water lost during hemodialysis by the use of a liquid membrane system comprising vesicles having a bilayer into which biochannels such as aquaporin water channels have been incorporated and wherein the vesicles further comprise a stabilising oil phase. In order to accomplish this it was suggested to create a salt gradient and a counter-current mimicking the normal kidney function across said liquid membrane, which will then constitute the necessary driving force for a forward osmosis processes. Talaat (Saudi J Kidney Dis. Transpl., 21(4):748-749, 2010) later proposed to use forward osmosis for dialysis fluid regeneration where theoretically up to 50% of spent dialysis fluid water may be retrieved. However, due to limitations on draw solutes such as salts and glucose, Talaat concludes that a modified dialysis therapy prescription such as a prolonged daily therapy is necessary, and he further proposes to use a multilayer FO plate and frame module to be specifically built for testing the hypotheses.

Thus, various energy consuming processes for water purification are needed, e.g. activated carbon filtration, ion exchange, reverse osmosis, ultrafiltration and the like, to remove unwanted and even toxic substances of mineral and organic origin from the purified water.

SUMMARY OF THE INVENTION

Accordingly, the present invention provides a system or apparatus for utilizing the water content in spent fluid (101), such as filtrate derived from a patient's blood or plasma during a renal replacement therapy process, said system or apparatus providing a flux of water from said spent fluid by forward osmosis.

The present invention achieves this with a system for recycling at least a part of the water content in waste fluid (507) from a hemofiltration process resulting in a flux of water from said waste fluid into a supply of electrolyte replacement concentrate (509) or into a stream of concentrated blood resulting from said hemofiltration (505), said system comprising a forward osmosis (FO) unit (102, 506) comprising a forward osmosis membrane (103) comprising nanoporous water channels, said membrane having a feed side (104) and a draw side (105) wherein the feed side is in fluid communication with said waste fluid (507) being the filtrate from a patient undergoing said hemofiltration, and wherein the draw side is in fluid communication with a supply of said electrolyte concentrate (509) or wherein the draw side is in fluid communication with a stream of concentrated blood resulting from said hemofiltration (505).

In addition, said system may comprise a forward osmosis (FO) unit (102) comprising a forward osmosis membrane (103) having a feed side (104) and a draw side (105), wherein the feed side is in fluid communication with filtrate waste fluid or spent fluid from a patient undergoing a renal replacement therapy; and wherein the draw side is in fluid communication with either a supply of dialysis concentrate, a supply of electrolyte replacement concentrate, or a flow of concentrated blood having undergone hemofiltration (106) or a combination of one or more of such sources, and where said forward osmosis membrane has an active layer which comprises nanoporous water channels such as aquaporin water channels. The FO unit may conveniently be in the form of a filter cartridge comprising a hollow fiber module. Such a module has the advantage of being compact and has a well-known form factor for use in hemofiltration apparatus. In addition, the module can be easy to replace after use in single use applications in continuos renal replacement therapies.

In a further aspect, the present invention provides the use of the system of the present invention for recycling at least a part of the water content in waste fluid from a hemofiltration process resulting in a flux of water from said waste fluid into a supply of electrolyte replacement concentrate or into a stream of concentrated blood resulting from said hemofiltration.

In a further aspect, the present invention provides a forward osmosis membrane comprising nanoporous water channels for use in a method of treating a patient undergoing a hemofiltration in the course of renal replacement therapy, wherein the membrane is part of a forward osmosis (FO) unit and has a feed side and a draw side, the feed side being in fluid communication with a waste fluid which is a filtrate from the patient and the draw side being in fluid communication with a supply of said electrolyte concentrate or a stream of concentrated blood resulting from the hemofiltration, so that a part of the water content in the waste fluid from the hemofiltration is recycled, resulting in a flux of water from the waste fluid into a supply of electrolyte replacement concentrate or into a stream of concentrated blood resulting from said hemofiltration. Accordingly, in this use of the forward osmosis membranes of the present invention, the membranes with nanoporous water channels are the component of the system that is consumed and changed between the treatment of different patients or temporally separated treatments of the same patient.

In a further aspect, the present invention provides a method of using the systems and apparatus described herein for recycling at least a part of the water content in waste fluid from a hemofiltration process. In one aspect, the present invention provides a method for recycling at least a part of the water content in waste fluid from a hemofiltration process resulting in a flux of water from said waste fluid into a supply of electrolyte replacement concentrate or into a stream of concentrated blood resulting from said hemofiltration, the method comprising providing a system of the present invention;
supplying to the system the waste fluid from a patient undergoing said hemofiltration to a feed side of a forward osmosis (FO) unit comprising a forward osmosis membrane comprising nanoporous water channels;
extracting filtrate from a draw side of the membrane of the forward osmosis (FO) unit, wherein the draw side is in fluid communication with a supply of said electrolyte concentrate or wherein the draw side is in fluid communication with a stream of concentrated blood resulting from said hemofiltration, thereby recycling at least a part of the water content in the waste fluid from the hemofiltration process.

Other objects of the invention will be apparent to the person skilled in the art from the following detailed description and examples.

The system of the invention for utilizing the pure water content in spent fluids, such as filtrates from hemofiltration therapy, may further provide means for water extraction from filtrates and spent dialysate fluids using a draw solution, such as a stream of concentrated blood and/or fresh replacement fluid or dialysate concentrate for forward osmosis water transport across a semipermeable membrane ideally only allowing $H_2O$ transportation through nanopores, e.g. such as the water channels of aquaporin proteins. The semipermeable forward osmosis membrane useful in the system of the invention would preferably have high salt rejection and high water flux, preferably combined with a low molecular weight cut-off, MWCO. Several new membrane preparation methods for forward osmosis applications have emerged, such as preparation of thin film composite (TFC) membranes with a customized polysulfone (PSI) support, electrospun support, TFC membranes on hydrophilic support and hollow fiber membranes, cf. review by Alsvik and Hagg (2013) who describes several FO membranes having high sodium chloride rejection rates of more than about 95% and high water flux. Advantages of the system of the present invention may include: reduced energy consumption for reverse osmosis (RO) and ultrafiltration (UF) water purification and reduced water consumption in renal replacement therapy through reuse of water from hemofiltration filtrate and/or spent dialysate fluids; as well as reduction of risk of body exposure to external toxins such as organic water pollutants and endotoxins. In addition, the use of the highly selective aquaporin membranes described herein may significantly reduce or eliminate reverse flux of low molecular weight metabolites and the like from the waste fluids during (osmotic) filtration processes, thus enabling the use of said aquaporin membranes in renal assist devices and artificial kidney as well as for the re-use of pure water from said spent or waste fluids.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Depending upon the material used for the forward osmosis (FO) units and the membrane(s) therein, the structure of the membrane(s), and the arrangement of the membrane(s) within the FO unit, the amount and rate of transfer of water may be enhanced and/or controlled. Furthermore, a plurality of membranes and/or FO units may be used and may operate in a parallel or serial flow configuration. Also the system may comprise recirculation of the draw and feed solutions within an FO unit in order to optimise water extraction.

The following drawings illustrate various concepts and embodiments of the invention showing functional elements by way of examples and not by limitation. It will be understood that implementations are not limited to the specific components disclosed herein, as virtually any components consistent with the intended operation of an organic forward osmosis system may be utilized.

BRIEF DESCRIPTION OF THE DRAWINGS

In FIG. 5A the reference number (509) is an electrolyte-containing replacement concentrate which enters the shell side surrounding the hollow fibers in (506) here functioning as the draw; (510) is the diluted electrolyte replacement concentrate (replacement fluid); (511) is an optional supply replacement fluid, such as isotonic replacement fluid.

In FIG. 5B reference number (503) is blood coming from the patient; (505) is the (partly dewatered) hemofiltered blood here passing to the shell side of the FO hollow fiber module (506) acting as the draw; (507) is filtrate from the hemofilter passing to the lumen side of the FO module; (504) is blood returning to the patient; (508) is dewatered hemofilter filtrate.

FIG. 5C additionally shows an optional electrolyte replacement solution (512) for predilution of the blood.

FIG. 5D additionally shows an optional electrolyte replacement solution (513) for postdilution of the blood.

FIG. 5E further shows an example of how pumps (514, 515, 516), such as peristaltic pumps, may conveniently be fitted into a system for water reuptake from the otherwise waste filtrate to provide and maintain a suitable flow of the fluids involved.

DETAILED DESCRIPTION OF THE INVENTION

Figure 5A:
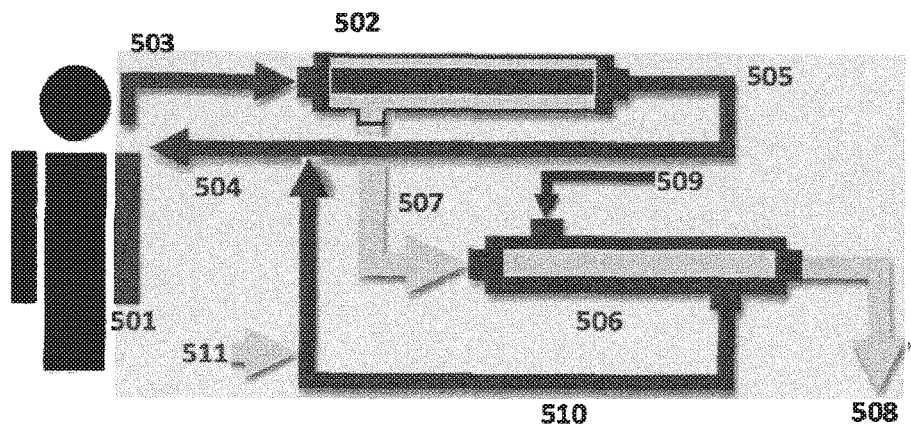
FIGS. 5A-5E show schematic diagrams of systems for re-use of water lost through hemofiltration in which: (501) is the patient undergoing hemofiltration; (502) is the hemofilter which commonly is a hollow fiber unit; (503) is blood coming from the patient and passing through the lumen of the hollow fibers; (504) is blood returning to the patient; (505) is the hemofiltered blood; (506) is a forward osmosis (FO) module shown in the form of a hollow fiber module; (507) is filtrate from the hemofilter passing to the lumen side of the FO module; (508) is dewatered hemofilter filtrate. Each of these systems may be integrated in an apparatus for hemofiltration as known in the art, cf. US patent application No. US2010/0121246.
Figure 5B:
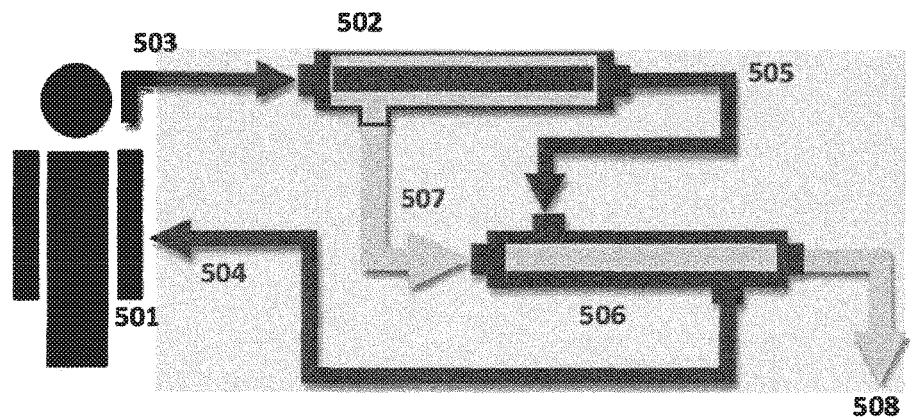

More specifically, the system of the present invention relates to a system or apparatus useful where said renal replacement therapy process is hemofiltration, the spent fluid is the filtrate (filtered plasma from a patient) from the hemofiltration (507), and the draw side of the FO unit is in fluid communication with a supply of electrolyte replacement concentrate (509), cf. FIG. 5A; or where the draw side of the FO unit is in fluid communication with a flow of blood having undergone hemofiltration (505) and has lost some of its water content through the hemofiltration, cf. FIG. 5B. In both instances the FO unit enables reabsorption of water lost from the blood during hemofiltration to either electrolyte replacement concentrate (FIG. 5A) or to the concentrated blood (FIG. 5B).

In the system of the present invention, it is preferred that the forward osmosis membrane comprises nanoporous water channels and thereby reducing or eliminating reabsorption of all or most other solutes from the spent fluid. Moreover, it is preferred that the FO unit of the system comprises a membrane comprising aquaporin water channels, which, due to their highly selective nature, only pass pure water molecules. The FO unit comprising the FO membrane having nanopores such as aquaporin water channels may be provided in the form of a filter cartridge which can be used as an add on in an apparatus as disclosed in the published patent application US 2010/0121246 A1 relating to a modular hemofiltration apparatus with interactive operator instructions and control system. FIGS. 5 and 6 therein schematically show components of the apparatus when configured for various therapies. In FIG. 5 the apparatus is set up for carrying out CVVHDF; In FIG. 6 the apparatus may be set up for carrying out CVVHDF. The subject matter relating to the provision of a hemofiltration system and apparatus of US 2010/0121246 A1 is incorporated hereinby reference.

Figure 2:
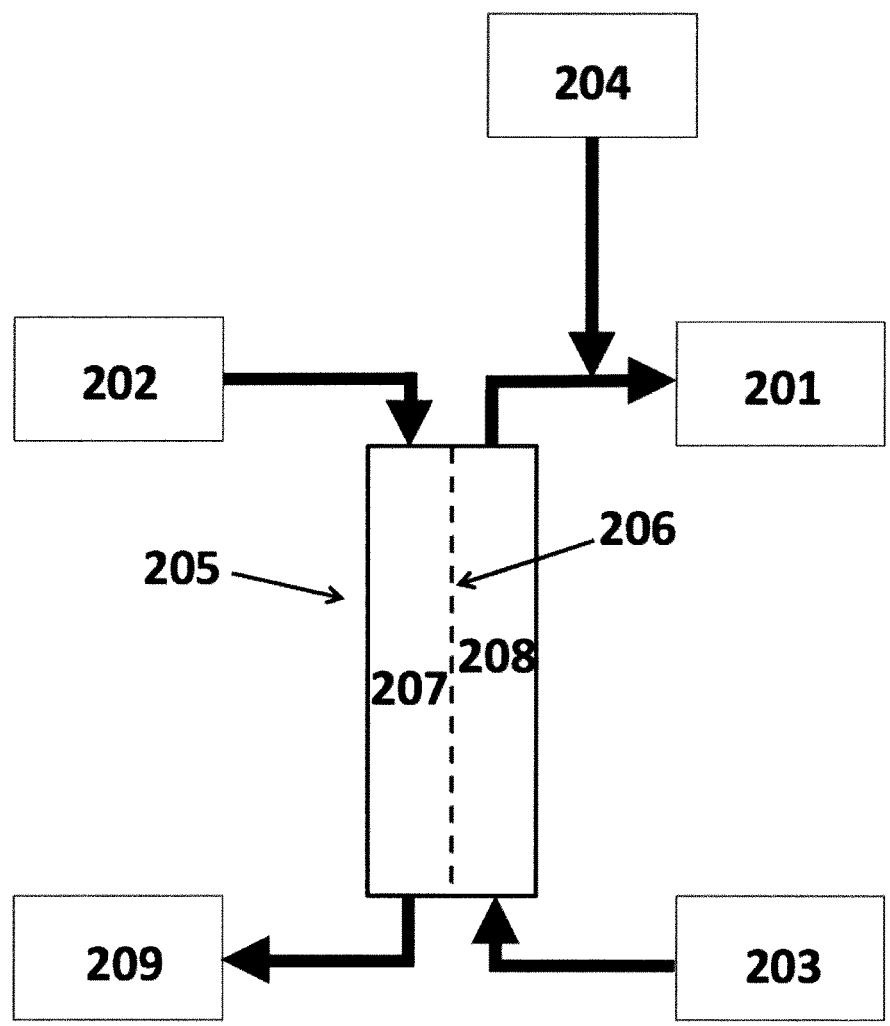
FIG. 2 shows a schematic diagram of a system according to the invention for preparing a fresh dialysate in which: (201) is the fresh dialysate; (202) is the spent dialysate; (203) is a supply of dialysis concentrate; (204) is a supply of purified water; (205) is a forward osmosis (FO) unit in which (206) is the forward osmosis (FO) membrane, (207) is the feed side and (208) is the draw side; (209) is the dewatered spent dialysate.

In the system of the present invention, for example as shown in FIG. 2, the renal replacement therapy process is dialysis; the spent fluid is the spent dialysate: and the draw side of the FO unit is in fluid communication with a supply of dialysis concentrate; and a system for preparing a fresh dialysate (201) by utilizing water of the spent dialysate (202), said system comprising i) a supply of dialysis concentrate (203); ii) a supply of purified water (204); and iii) a forward osmosis (FO) unit (205) comprising a forward osmosis membrane (206) having a feed side (207) and a draw side (208), wherein the feed side is in fluid communication with spent dialysate from a patient undergoing dialysis; and wherein the draw side is in fluid communication with the supply of dialysis concentrate. These embodiments provide the possibility of recycling at least a part of the water content of a spent dialysate solution for direct dilution of dialysate concentrates, said water being originally of a highly purified quality in order to avoid transmission of toxic or pyrogenic substances to the blood of a patient undergoing dialysis.

In addition, the system of the invention may be useful in at least partly recycling the purified water used in preparing dialysates for peritoneal dialysis.

It is preferred that said membrane comprises
  an active layer comprising immobilized aquaporin water channels, and
  a support layer, and
that said active layer is a cross linked aromatic amide layer, preferably formed by interfacial polymerization, wherein aquaporin vesicles are incorporated, said vesicles being formed by self assembly of amphiphilic matrix forming compounds in the presence of an aquaporin protein preparation. Membranes prepared in this way have proven to be robust, have high water transport capacity and low to very low reverse flux of salt and low molecular weight substances.

In certain embodiments of the present invention, the amphiphilic matrix forming compounds are selected from an amphiphilic lipid, a hydrophobin, a diblock copolymer, a triblock copolymer or mixtures thereof, and said aquaporin water channel is selected from aquaporins of procaryotic origin, e.g. AqpZ; mammalian aquaporins, e.g. Aqp1 and Aqp2; plant aquaporins including Plasma intrinsic proteins (PIP), Tonoplast intrinsic proteins (TIP), Nodulin intrinsic proteins (NIP), and Small intrinsic proteins (SIP) e.g. SoPIP2; 1, PttPIP2; 5 and PtPIP2; 2; yeast aquaporins e.g. AQY1 and AQY2; as well as the aquaglyceroporins such as GlpF and Yfl054.

In some embodiments of the system of the present invention, the system comprises more than one, such as two or three forward osmosis units. This configuration is useful where more than one dialysate concentrate is needed to prepare the final fresh dialysate solution.

In further aspects, the present invention provides a method for preparing a fresh dialysate solution for dialysis by reusing part of a spent dialysate comprising extracting pure water by use of forward osmosis from the spent dialysate from a patient undergoing hemodialysis. In particular, this may involve use of the spent dialysate as the feed solution in the forward osmosis process; and a dialysate concentrate constitutes the draw solution in the forward osmosis process. The use of highly purified water, such as through one or more ultrafiltration steps, as well as sterilization filtration steps, for the preparation of the fresh dialysate would be greatly reduced using this method, thus saving energy, devices, and space among other advantages.

In addition, this method, in which the forward osmosis process is used for extracting pure water, may involve the use of a pressure assisted forward osmosis process, e.g. to increase water flux or filtration speed. This could be achieved by further including means for pressurizing said feed streams in the system of the invention, e.g. to enable the application of a slight pressure, such as by pumping or using gravity and the like, on the feed side of the aquaporin containing membrane (using the concept of assisted forward osmosis).

Figure 5C:
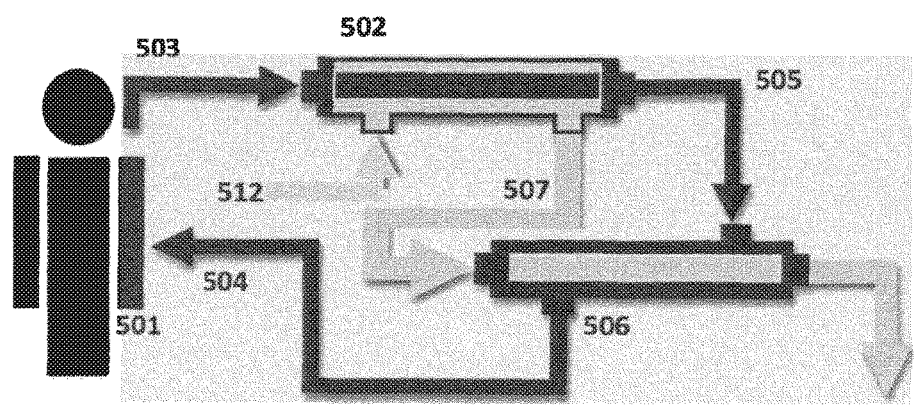
Figure 5D:
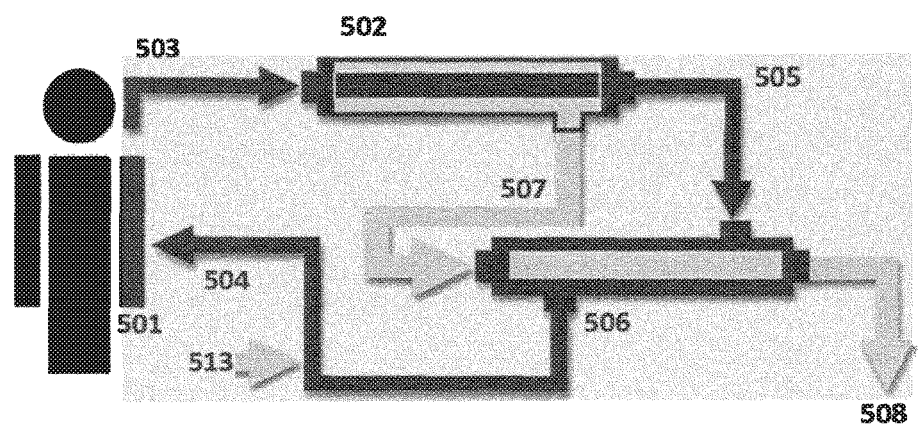
Figure 6:
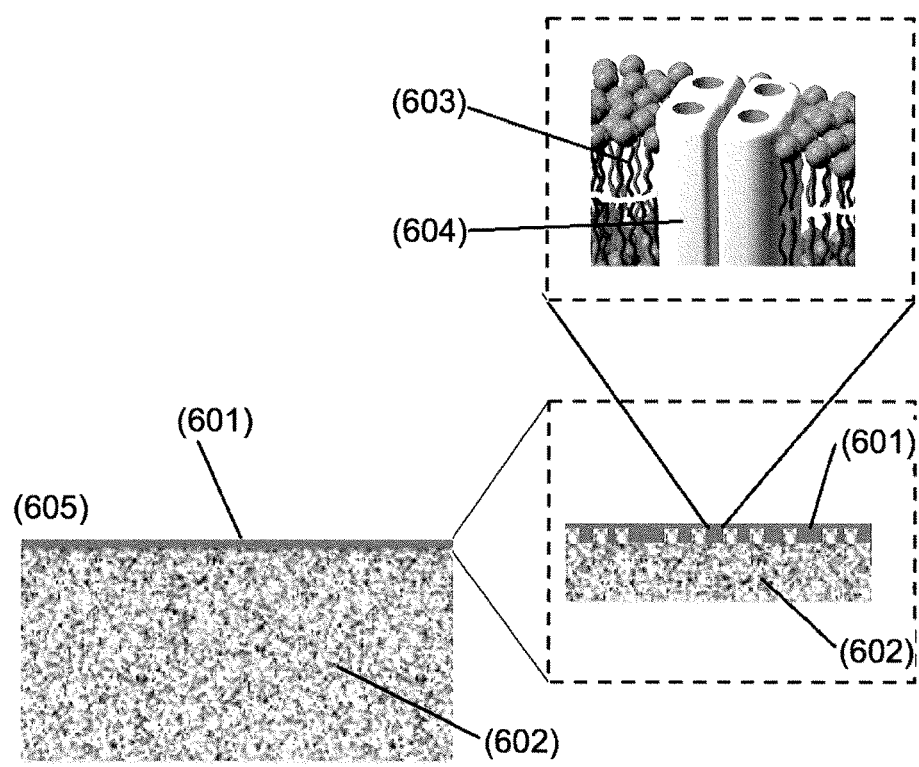
FIG. 6 shows a principle sketch of the microstructure of a membrane material (605) of the TFC type with the thin film composite layer formed on a hollow fiber or flat sheet aquaporin membrane wherein (601) refers to the TFC layer; (602) refers to the support membrane; (603) schematically represents the bilayer membrane of a vesicle; (604) is the aquaporin protein in its tetrameric form.

In a further aspect, the present invention also relates to a dialysis machine comprising the system for preparing a fresh dialysate solution as described above, and a renal assist device (506) as shown in FIGS. 5C and 5D.

Definitions, Explanations and Embodiments of the Invention

Hemofiltration machines, Hemodialysis machines, dialyzers and replacement fluids, concentrates and solutions for hemofiltration, hemodiafiltration and dialysis are manufactured and sold by a number of companies including Omniflo (subsidiary of Transvivo Inc. Napa, Calif., USA), Fresenius Medical Care (fmc-ag.com), Gambro (gambro.com) (now part of Baxter), Nipro (nipro.com), nxStage (nxstage.com) and Bellco (bellco.net).

In hemodialysis, the dialyzer functions partly as an artificial kidney. The dialyzer is typical in the form of a hollow fibre module with a bundle of hollow fibres (such as up to 20,000 fibres). The lumen of the hollow fibres form the "blood compartment" of the dialyzer and the space surrounding the fibres form the "dialysate compartment".

In peritoneal dialysis, the peritoneum in connection with the infused dialysate functions partly as an artificial kidney and the patient's peritoneal membrane functions as a semipermeable membrane across which fluids and dissolved substances are exchanged from the blood. Fresh hyperosmotic dialysate solution is introduced through a permanent tube into the abdominal cavity and spent dialysate is flushed out either every night while the patient sleeps (automatic peritoneal dialysis) or via regular exchanges throughout the day (continuous ambulatory peritoneal dialysis).

The actual composition of a hemofiltration filtrate or ultrafiltrate or a spent dialysate solution varies from patient to patient and from time to time. Metabolic changes appear in patients suffering from kidney failure resulting in elevated urea levels in the patient's blood plasma along with elevated levels of toxic metabolites such as indoles, phenoles, hormones, oxalate and protein degradation products, cf. Table 1 below.

TABLE 1

Metabolic wastes in spent dialysate, Kupcinskas (2000)

| Substances | Example (if applicable) |
|---|---|
| Urea | |
| Guanidines | Methylguanidine, guanidine, β-guanidinopropionic acid, Guanidinosuccinic acid, γ-guanidinobutyric acid, Taurocyamine, Creatinine, Creatine, Arginic acid, Homoarginine, N-α-acetylarginine |
| Phenols | o-cresol, p-cresol, benzyl alcohol, phenol, tyrosine |
| Phenolic acids | P-Hydroxyphenylacetic acid, β-(m-Hydroxyphenyl)-Hydracrylic acid |
| Hippurates | p-Hydroxyhippuric acid, o-Hydroxhippuric acid, Hippuric acid |
| Benzoates | Benzoic acid |
| Polypeptides | |
| β2-micro-globulin | |
| Indoles | Indol-3-acetic acid, Indoxyl sulfate, 5-Hydroxyindol acetic acid, Indol-3-acrylic acid, 5-Hydroxtryptophol, N-acetyltryptophan, Tryptophan |
| Ammonia | |
| Alkaloids | |
| Trace metals | Bromine |
| Uric acid | |
| Cyclic AMP | |
| Amino acids | Glycine, Leucine, Cysteine, Arginine |
| Myoinisitol | |
| Mannitol | |
| Oxalate | |
| Glucuronate | |
| Glycols | Glycolic acid |
| Lysozyme | |
| Hormones | Parathormone, Natriuretic Factor, Glucagon, Growth Hormone, Gastrin, Prolactin, Catecholamines |
| Xanthines | Xanthine, Hypoxanthine |
| Furanpropionic acid | |
| Amines | Putrescine, Spermine, Spermidine, Dimethylamine, Polyamines |
| Endorphines | |
| Pseudouridin | |

The substances mentioned in Table 1 may be used singly or in combination for the preparation of a model "spent dialysate", cf. Example 8.

In addition, hemofiltration is a renal replacement therapy used in intensive care, such as for acute renal failure. It is a slow continuous therapy in which sessions usually last between 12 to 24 hours and are usually performed daily. During hemofiltration, a patient's blood is passed via a machine to a semipermeable membrane, typically an ultrafiltration membrane, for removal of waste products and excess water. Examples of hemofiltration therapies as used herein include CVVH (continuous veno-venous hemofiltration) and CAVH (continuous arteriovenous hemofiltration), SCUF (slow continuous ultrafiltration), CVVHFD (continuous high flux dialysis), HVHF (high volume hemofiltration), cf. also Ronco, C. (2006) Critical Care 10:123 (doi:10.1186/cc4843). Use of the system of the present invention in a hemofiltration setting is described below in Example 7.

Hemofiltration is sometimes used in combination with hemodialysis, when it is termed "hemodiafiltration", as used in the CVVHDF therapy of continuous veno-venous hemodiafiltration. Blood is pumped through the blood compartment of a high flux dialyzer, and a high rate of ultrafiltration is used, so there is a high rate of movement of water and solutes from blood to dialysate that must be replaced by substitution fluid that is infused directly into the blood line. However, dialysis solution also runs through the dialysate compartment of the dialyzer. The combination is theoretically useful because it results in good removal of both large and small molecular weight solutes.

The term "spent fluid" or "waste fluid" as used herein include filtrate fluid from hemofiltration and spent dialysate from hemodialysis, and spent fluid (dwell) from peritoneal dialysis. The spent fluid is typically diluted during the various renal replacement therapies with water stemming from the blood, plasma, tissue and cells of the patient undergoing said therapy. Spent fluid represents an aqueous drainage fluid containing metabolic waste which is discarded continuously during hemofiltration, hemodiafiltration, and hemodialysis, or which is discarded as a batch following a peritoneal dialysis session.

"FO unit" as used herein refers to a closed housing comprising a semipermeable membrane separating two compartments or regions for i) a preferably aqueous feed solution having relatively low osmolarity or osmotic pressure, and ii) a preferably aqueous draw solution having an osmolarity or osmotic pressure which is higher than that of the feed solution. The FO unit has separate inlets and outlets for said feed and draw solutions. The FO unit may be of the flat sheet type or hollow fiber type. When the FO unit is of the hollow fiber type the two compartments or regions are variously designated as lumen and shellside space (or extracapillary space), or as lumen side (or tubeside) and shell side.

The term "assisted forward osmosis" (AFO) (or "pressure assisted forward osmosis", PAFO) as used herein refers to the concept of applying a mechanical (hydraulic) pressure to the feed side of the membrane to enhance the water flux through synergising the osmotic and hydraulic driving forces. This could be achieved by applying a slight pressure on the feed side of the nanoporous water channels containing membrane (using the concept of assisted forward osmosis). The additional driving force provides an increase in permeation flux. The concept of AFO is described in further detail in e.g. Blandin et al (2013), Validation of assisted forward osmosis (AFO) process: Impact of hydraulic pressure, Journal of Membrane Science, 447, 1-11.

The term "amphiphilic matrix forming compounds" as used herein comprises lipids such as phospholipids; block copolymers having both hydrophilic (A, C) and hydrophobic (B) blocks such as A-B, A-B-A and A-B—C types, and hydrophobins (both class I and class II) that are useful in the preparation of membranes, such as bilayer membranes, and the like. The amphiphilic matric forming compounds preferably form bilayer-like planar or vesicular membranes of the lipid membrane type or the block copolymer A-B::B-A, A-B-A and A-B—C types for incorporation of transmembrane proteins. Some amphiphilic matrix forming compounds may be included in smaller amounts the membranes, e.g. detergents such as poloxamers and hydrophobins.

"Purified water": Water purity for dialysis is of critical importance for patient health. Thus, the water used according to the present invention for supplementing the utilized water of the uses dialysate must be of the high purity normally used in preparation of dialysate solutions.

Dialysate Concentrates

A variety of concentrate formulations for preparing dialysate solutions for hemodialysis or peritoneal dialysis are well known in the art. These formulations vary not only with respect to specific constituents but also with respect to the concentration of these constituents. Generally, concentrate formulations include sodium chloride as the major constituent and potassium chloride, calcium chloride and magnesium chloride as minor substituents. Also dextrose (glucose) may be included.

Sodium acetate and/or sodium bicarbonate are also included as a buffer source to correct for metabolic acidosis. With acetate buffer, all of the constituents can be combined into a single concentrate. With bicarbonate buffer, two concentrates are necessary to prevent the precipitation of calcium and magnesium as carbonate salts.

Conventional two-part bicarbonate-based dialysis solutions are prepared by mixing an "acid" concentrate, a "base" concentrate and water. Normally the acid concentrate includes all of the acid, dextrose, calcium, magnesium, potassium and some portion of the physiologic requirement for sodium chloride whereas the base concentrate includes sodium bicarbonate and the balance of the required sodium chloride. In some commercial formulations of dialysate concentrates, the sodium chloride content of the base concentrate is zero. Since acetic acid is a liquid at room temperature, most of the acid concentrates using acetic acid are liquid products; whereas the base concentrates are produced both as powder and liquid concentrates. Many other combinations of acid and base concentrates that are commercially available are specific to the dialysis solution preparation methods and delivery equipment.

Specific examples of dialysate concentrate systems are (in brackets are mentioned the dilution ratios as volume of acid concentrate to volume of base concentrate to volume of water) the Renasol® bicarbonate hemodialysis concentrate series (1:1.83:34) and the Centrisol® hemodialysis concentrate series (1:1.72:42.28) from Medivators (www-medivators.com) (formerly Minntech), the NaturaLyte® Liquid Acid Concentrates series (1:1.72:42.28) and the Citrasate® Citric Acid Concentrate series (1:1.72:42.28) from Fresenius Medical Care, the RenalPure® Liquid Acid Concentrate/SteriLyte® series (1:1.83:34, 1:1.72:42.28 and 1:1.225:32.775) from Rockwell Medical (www-rockwellmed.com) and the BiCart Select® Citrate series (1:ca 2:197) from Gambro (www.gambro.com).

Hemofiltration Concentrates

Likewise, a variety of substitution solutions for hemofiltration and concentrate formulations for preparing substitution solution for hemofiltration are well known in the art. Besides the contribution to the removal of uraemic toxins and the correction of the patient's fluid status, hemofiltration solutions also correct the acid-base-balance of the patient. As renal failure leads to an exhaustion of the buffer systems and, consequently, to the development of metabolic acidosis, the net administration of buffer base is required. Specific examples are the Normocarb HF™ 25 and 35 electrolyte concentrates from Dialysis Solutions Inc. (www.normocarb.com).

Forward Osmosis Membrane

The forward osmosis membrane for use in the system and method according to the present invention may be any membrane suitable for forward osmosis. Many types of semi-permeable membranes are suitable for this purpose provided that they are capable of allowing the passage of the solvent, while blocking the passage of the solutes and not reacting with the solutes in the solution.

The membrane can have a variety of configurations, including thin films, hollow fibers and tubes, spiral wound, monofilaments and disk tubes.

In some embodiments, membranes made of materials such as cellulose acetate (CA), cellulose nitrate, polysulfone, polyvinylidene fluoride, polyamide (PA) and acrylonitrile co-polymers may be used. Other membranes may be mineral membranes or ceramic membranes made of materials such as $ZrO_2$ and $TiO_2$.

In further embodiments, the membrane may be an asymmetric membrane with an active layer—being the rejecting layer—and a supporting layer for supporting the active layer. In a further embodiment, the membrane may be a TFC (thin film composite) membrane. The thin film polyamide layer may be formed by an interfacial polycondensation reaction between polyfunctional amine (e.g. m-phenylenediamine, MPD) and polyfunctional acyl halide (e.g. trimesoyl chloride, TMC) monomers which are sequentially coated upon the support from immiscible solutions.

In a further embodiment the membrane is configured to selectively pass species through the semipermeable membrane by size, by excluding the ions or the solute from passing through the semi-permeable membrane while allowing water to pass through the semipermeable membrane.

In a further embodiment the various layers of the membrane may be modified to improve the flux and/or rejection properties, including reducing reverse draw flux phenomena. Examples of such improvements are described in WO2014/075086.

In a special embodiment, the membrane may comprise nanoporous water channels, such as nanoparticles, nanotubes, carbon nanotubes, graphene based materials, aquaporin water channels and/or biomimetic synthetic water selective porous material.

Commercial forward osmosis membranes may eg. be obtained from Hydration Technology Inventions LLC (HTI) (www.htiwater.com) and Aquaporin A/S (www.aquaporin.dk).

Membrane Material Comprising Aquaporin Water Channels.

With reference to FIG. 6, the membrane material (605) comprises an active layer (601) comprising aquaporin water channels, such as protein tetramers in immobilized form. In some embodiments, the membrane material (605) further comprises a support layer (602).

In some embodiments, the active layer comprising immobilized aquaporin water channels is a cross linked aromatic amide thin film, wherein aquaporin containing vesicles are incorporated. Here a section of a vesicle having an aquaporin tetramer incorporated in a lipid bilayer is shown.

In some embodiments, the aquaporin containing vesicles are formed by self assembly of amphiphilic lipids or block copolymers or a mixture thereof in the presence of an aquaporin protein suspension.

The active layer comprising immobilized aquaporin water channels may further comprise a thin film composite (TFC) layer that serves to immobilise the aquaporin water channels.

In some embodiments, the active layer comprising immobilized aquaporin water channels is a cross linked aromatic amide thin film, wherein aquaporin containing vesicles are incorporated.

In some embodiments, the support layer is a polysulfone or polyether sulfone support membrane.

"Aquaporin water channel" as used herein refers to selective water channel proteins, including AqpZ and SoPIP2; 1 prepared according to the methods described by Maria Karlsson et al. (FEBS Letters 537 (2003) 68-72) or as described in Jensen et al. US 2012/0080377 A1.

The "active layer comprising immobilized aquaporin water channels" is a layer wherein the aquaporin water channels are immobilized, such as or more or less embedded or partly embedded in or even supported in or on said active layer. Said active layer is preferably created in close contact with a support layer, such as a typical polysulfone or polyether sulfone support membrane.

Formation of a separation layer in the form of a thin film layer as known in the art onto the surface of a support membrane results in changes to the water transport mechanism. Instead of water transport taking place by normal diffusion through the pores of the support membrane, another type of water transport takes place through the thin film layer as is known from this type of reverse osmosis membranes, where membrane permeability is limited. The nonporous nature of the thin film separating layer results in transport of water requiring "jump diffusion" as described in Kotelyanskii et al. 1998. Thus, thin film modification of water membranes have mainly found use in reverse osmosis, where a hydrostatic pressure is required to force the water through the membrane, and the obtained advantage lies in the improved separation of unwanted solutes in the water to be filtered. These conventional membranes for reverse osmosis have effectively 100-200 nm thick non-porous layers supported by a porous material. Water permeation in these membranes occurs as a diffusion process through the non-porous layer established via the appearance and disappearance of interstitial spaces. The active layer used in the present invention is further improved relative to the prior art thin film membranes by having aquaporin water channels incorporated in the thin film layer making it a thin film composite (TFC) layer. The incorporation of aquaporins have the added benefit of providing a selective water transport through its pores having a diameter of only 2.4 Å at its narrowest passage (AqpZ pore, cf. Wang et al. 2005) where an efficient single file water transport takes place.

"Thin-film-composite" or (TFC) membranes as used herein refers to a thin film membrane active layer, said layer being prepared using an amine reactant, preferably an aromatic amine, such as a diamine or triamine, e.g. 1,3-diaminobenzene (m-Phenylenediamine>99%, e.g. as purchased from Sigma-Aldrich) in an aqueous solution, and an acyl halide reactant, such as a di- or triacid chloride, preferably an aromatic acyl halide, e.g. benzene-1,3,5-tricarbonyl chloride (CAS No. 84270-84-8, trimesoyl chloride (TMC), 98%, e.g. as purchased from Sigma-Aldrich) dissolved in an organic solvent where said reactants combine in an interfacial polymerization reaction, cf. U.S. Pat. No. 4,277,344 which describes in detail the formation of a polyamide thin film formed at the surface of a porous membrane support, e.g. a polyethersulfone membrane. More specifically, benzene-1,3,5-tricarbonyl chloride can be dissolved in a solvent, such as a C6-C12 hydrocarbon including hexane (>99.9%, Fisher Chemicals), heptane, octane, nonane, decane etc. (straight chain or branched hydrocarbons) or other low aromatic hydrocarbon solvent, e.g. Isopar™ G Fluid which is produced from petroleum-based raw materials treated with hydrogen in the presence of a catalyst to produce a low odor fluid the major components of which include isoalkanes. Isopar™ G Fluid: Chemical Name: Hydrocarbons, C10-C12, isoalkanes, <2% aromatics; CAS No: 64742-48-9, chemical name: Naphtha (petroleum), hydrotreated heavy (from ExxonMobil Chemical). Alternatives to the reactant 1,3-diaminobenzene include diamines such as hexamethylenediamine etc., and alternatives to the reactant benzene-1,3,5-tricarbonyl chloride include a diacid chloride, adipoyl chloride etc. as known in the art. To make the active layer a thin film composite layer, an additional component, herein aquaporin water channels, that facilitates water transport are added to the reactant solutions before interfacial polymerization takes place. Said component may or may not participate in the reaction, but preferably is inert to the reaction and becomes immobilised in the thin film formed.

The Vesicles

In some embodiments, the aquaporin water channels are incorporated in vesicles before incorporation into the active layer, such as the TFC layer. In some embodiments, the vesicles into which the aquaporin water channels are incorporated are liposomes or polymersomes.

In some embodiments, TFC layer is formed through interfacial polymerization of an aqueous solution of a di- or triamine with a solution of di- or triacyl halide in an organic solvent, and wherein the aquaporin water channel vesicles are incorporated in said aqueous solution.

By way of example, the membrane may be manufactured at described by Zhao, Y. et al (2012).

The liposomes are prepared from lipids such as DPhPC, DOPC, mixed soybean lipids, or *E. coli* mixed lipids. One example of a soybean lipid mixture is asolectin. "Asolectin" as used herein refers to a soybean lecithin fraction [IV-S], which is a highly purified phospholipid product containing lecithin, cephalin, inositol phosphatides and soybean oil (synonym: azolectin). "Proteoliposomes" as used herein are vesicles that typically have a lipid to protein ratio (LPR calculated on a mole basis) of between 25 to 500, such as about 100 to about 200.

In some embodiments, the polymersomes may comprise triblock copolymers of the hydrophile-hydrophobe-hydrophile (A-B-A or A-B-C) type or diblock copolymers of the hydrophile-hydrophobe type (A-B). In some embodiments, said polymersomes may comprise a combination of triblock copolymers of the hydrophile-hydrophobe-hydrophile type and diblock copolymers of the hydrophile-hydrophobe type.

"Proteopolymersomes" as used herein are vesicles that typically have a polymer to protein ratio (POPR calculated on a molar basis) of between 25 to 500, such as about 50 to about 100 when using a triblock copolymer and a polymer to protein ratio of between 25 to 500, such as about 100 to about 200 when using a diblock copolymer.

Commonly used block copolymers for membrane protein incorporation may be triblock copolymers, such as Polymethyloxazoline-Polydimethylsiloxane-Polymethyloxazoline ($PMOXA_n$-$PDMS_m$-$PMOXA_n$), where n and m represent the number of the monomer blocks. In aqueous solution, they self-assemble to bilayer sheets that close up to hollow spheres, called vesicles or polymersomes. The hydrophilic PMOXA faces towards the water, whereas the hydrophobic PDMS is located in the inside of the bilayer. Most relevant polymer-related parameters known so far for incorporation of transmembrane proteins (TM proteins) including aquaporins are: the molecular weight ($M_w$, the weight of one mol—$6*10^{23}$ molecules—polymers) and the hydrophilic volume ratio ($f_{phil(vol)}$, the ratio between volume of the hydrophilic blocks, meaning all blocks on both sides, and the volume of the complete polymer). The $M_w$ of PMOXA-PDMS-PMOXA triblock copolymers that has been shown to successfully incorporate membrane proteins including aquaporins is in the range between 4000 and 11000 g/mol. The $f_{phil(vol)}$ has been found so far to be between 0.15 and 0.45 (above and below these values, no vesicles can form). Recently, successful working polymers include: Diblock copolymers, made of Polybutadiene-Polyethylene oxide ($PB_m$-$PEO_n$) where PB is hydrophobic and PEO is hydrophilic, and where two molecules form a bilayer. The Mw of successfully TM protein incorporating $PB_m$-$PEO_n$ polymer was around 1200 g/ml and $f_{phil(vol)}$ around 0.3.

These and other polymers that are capable of self-assembling to polymersomes are listed in table 2 below.

TABLE 2

Polymers capable of self-assembly

| Chemistries | Source | Comment |
| --- | --- | --- |
| PB-PEO (Polybutadiene-Polyethylene oxide) | Discher, 2002 | Robust vesicles in aqueous solution |
| PAA-PS (Polyacrylic acid-polystyrene) | Discher, 2002 | Long PS chains (500) lead to solvent-selective vesicles (bilayer thickness = 20-40 nm) |
| PS-poly(isocyano-L-alanine-L-alanine) | Discher, 2002 Discher, 2000 | Vesicles & rods in acidic conditions diameter d = 10-100 nm, bilayer thickness = 16 nm |
| PEE-PEO (Polyethylethylene-Polyethylene oxide) | Discher, 2002, Discher, 2000 | Robust vesicles in aqueous solution in coexistence with spherical and wormlike micelles |
| PMOXA-PDMS-PMOXA (Polymethyloxazoline-Polydimethylsiloxane-Polymethyloxazoline) | Nardin, 2000 | Robust vesicles in aqueous solution |
| PEO-PPS (Polyethylene oxide-Poly(propylenesulfide)) | Discher, 2002 | |
| PEO-PLA (Polyethylene oxide-polylactide) | Discher, 2002 | Only micelles, potentially interesting for drug delivery |
| PEO-PS | Discher, 2000 | Stable vesicles (bilayer thickness = 20-25 nm) after dialysis from organic solvent to water |
| PEO-PMPS (PEO-Polymethylphenylsilane) | Discher, 2000 | Formed vesicles with highest PDI (1, 6); Hydrophobic layer thickness = 8-12 nm |

TABLE 2-continued

Polymers capable of self-assembly

| Chemistries | Source | Comment |
| --- | --- | --- |
| PCEMA (Poly(2-cinnamoylethyl methacrylate)) | Discher, 2000 | Water-soluble dye-loadable nanosphere (bilayer thickness = 20 nm) |
| PC-diC_18 (Phosphocholine-diC_18) | Discher, 2000 | |
| PIAA-PS (Polyisocyanoalanyl-alanyl methyl ester-PS) | Discher, 2000 | |
| PSSH-PEE (Polystyrene sulfonic acid-PEE) | Discher, 2000 | Best performing vesicles around 30 kDa, collapsed vesicles (d = 100 nm) and micelles in 0-1M NaCl |
| PEO-PPO-PEO (PEO-Poly(phenylene oxide)-PEO) | Discher, 2000 | Small vesicles, lifetime of a few hours (PEO bilayer thickness = 3-5 nm, PO bilayer thickness = 25 nm) |
| PS-PB | Discher, 2000 | Uni- and multilamellar vesicles in submicron range |
| PS-PPI (PS-Poly(propyl imine) | Discher, 2000 | Multilamellar vesicles in organic solution –> precipitate in water |
| PB-P2VP (PB-Poly(2-vinyl-pyridine) | Discher, 2000 | Multilamellar vesicles in aqueous solution, d = 150 nm |
| PPQ-PS (Poly((phenylquinolyne)-PS) | Discher, 2000 | Collapsed vesicles/Vesicle aggregates (bilayer thickness = 200 nm) in TFA/CHCl$_3$ |
| PBO-PEO (Polybutyloxide-PEO) | Harris, 2002 | Vesicles with nearly perfect bilayer structure |

Other examples of useful diblock copolymers and examples of useful triblock copolymers are listed in table 3 wherein EO-block-DMS-block represents poly(dimethylsiloxane-block-ethylene oxide-block), EO-block-BO-block represents poly(butylene oxide-block-ethylene oxide-block), and MOXA-block-DMS-block-MOXA-block represents poly(2-methyl-oxazoline-block-dimethylsiloxane-block-2-methyloxazoline).

TABLE 3

Di- and triblock copolymers (all from the supplier Polymer Source)

| Species | Formula | $n_{(hydrophobic)}$ | $n_{(hydrophilic)}$ |
| --- | --- | --- | --- |
| P7258 | EO$_{48}$DMS$_{70}$ | 70 | 48 |
| P5809 | EO$_{15}$BO$_{16}$ | 15 | 16 |
| P8365 | EO$_{25}$DMS$_8$ | 8 | 25 |
| P7259 | EO$_{48}$DMS$_{14}$ | 14 | 48 |
| P7261 | EO$_{114}$DMS$_{14}$ | 14 | 114 |
| P3691B | MOXA$_6$DMS$_{35}$MOXA$_6$ | 35 | 12 |
| P8061 | MOXA$_{15}$DMS$_{67}$MOXA$_{15}$ | 67 | 30 |
| P9548 | MOXA$_{15}$DMS$_{119}$MOXA$_{15}$ | 119 | 30 |

The "support layer" or support substrate functioning as membrane support may be e.g. a polyethersulfone membrane, such as the porous PES support membrane, e.g. a MICROPES 1FPH or 2FPH membrane from Membrana GmbH. Other examples of support layers that may be suitable include, but are not limited to, a cellulose acetate substrate, a nitrocellulose substrate, a cellulose esters substrate, a polycarbonate substrate, a polyamine substrate, a polyimide substrate, a polysulfone substrate, a polyether sulfone substrate, a polyacrilonitrile substrate, a polyethylene substrate, a polypropylene substrate, a polytetrafluoroethylene substrate, a polyvinylidene fluoride substrate, a polyvinylchloride substrate, a polyterepthalate substrate, an aluminium oxide substrate, a titanium oxide substrate, a zirconium dioxide substrate, a perovskite-type oxides substrate and mixtures thereof.

Examples of hollow fibre membranes suitable as support layer may be the MicroPES® capillary membranes (such as type TF10 etc) from Membrana GmbH.

Membrane Orientation

In forward osmosis processes the membrane orientation may be of importance. Thus, in one embodiment of the forward osmosis membrane module of the invention, the active layer faces the feed solution. This orientation is also called the FO mode. In a further embodiment of the module, the active layer faces the draw solution. This orientation is also called the PRO mode.

"Osmotic pressure" is the pressure that must be applied to prevent the net flow of solvent through a semipermeable membrane from a solution of lower solute concentration to a solution of higher solute concentration.

The osmotic pressure of a solution depends on the amount of particles in the solution. For an ideal solution the osmotic pressure is directly proportional to the molality.

"Osmolality" is a measure of the moles (or osmoles) of osmotic active solutes per kilogram of solvent, expressed as osmole/kg. The osmolality of an ideal solution of a non-dissociated compound equals the molality.

Osmolality is typically measured by freezing point depression. A one osmol/kg aqueous solution has a freezing point of −1.858° C. As an example: a 1 mol solution of eg sugar in 1 kg of water lowers the freezing point with 1.858° C. whereas the freezing point depression will be obtained by 0.5 mol in 1 kg of water.

"Osmolarity" is a measure of the osmoles of solute per liter of solution.

The "osmotic pressure" can be calculated from the osmolality by using the formula:

$$\pi(bar) = osmolality\left(\frac{osmole}{L}\right) \times R \times T(K)$$

wherein R is the gas constant (8.3144621 L bar K$^{-1}$ mol$^{-1}$).

EXPERIMENTAL SECTION

Example 1. Osmotic Potentials of Dialysate Concentrates Vs Ready Dialysates

The osmotic pressure of one example of an acid and a basic (bicarbonate) concentrate and the resulting ready-to-use dialysate was calculated using OLI Analyzer Studio 9.0 (OLI Systems Inc., NJ, US). In the calculated example, 1 L of the liquid acid concentrate is to be mixed with 1.575 L of bicarbonate concentrate and 42.425 L of purified water to give 45 L of ready-to-use dialysate. Table 4 gives the compositions of the three liquids and Table 5 shows the calculated osmotic pressures.

TABLE 4

Compositions of the liquids

| Composition Liquid | Na+ (mmol/L) | K+ (mmol/L) | Ca2+ (mmol/L) | Mg2+ (mmol/L) | Cl- (mmol/L) | HCO3- (mmol/L) | Acetate (mmol/L) | Glucose (g/L) |
|---|---|---|---|---|---|---|---|---|
| Acid concentrate | 4770 | 135 | 67.5 | 22.5 | 4950 | | 135 | 45 |
| Bicarbonate concentrate | 1000 | | | | | 1000 | | |
| Ready-to-use dialysate | 138 | 3.0 | 1.5 | 0.5 | 110 | 32 | 3.0 | 1.0 |

TABLE 5

Estimated osmotic pressures

| Liquid | Osmotic Pressure (bar) (at 37° C.) |
|---|---|
| Acid concentrate | 412 |
| Basic concentrate | 40 |
| Ready-to-use dialysate | 8 |

The spent dialysate will typically have a slightly lower osmotic pressure than the ready-to use dialysate due to excess body water extracted from the patient's blood. Thus, as can be seen from table 5, the acid and the basic concentrates both provide useful positive osmotic potential differences relative to the spent dialysate in a forward osmotic process extracting water from spent dialysate.

Example 1b. Osmotic Potentials of Replacement Fluid Concentrates Vs Ready Replacement Fluids The osmotic pressures of two examples of replacement fluid concentrates and the resulting ready-to-use replacement fluids were calculated using OLI Analyzer Studio 9.0 (OLI Systems Inc., NJ, US).

In the calculated examples, 0.240 L of the concentrate is to be mixed with 3 L of purified water to give 3.24 L of infusate solution.

Table 4b gives the compositions of the three liquids and Table 5b shows the calculated osmotic pressures.

TABLE 4b

Compositions of the liquids

| Composition Liquid | NaCl (g/L) | MgCl$_2$·6H$_2$O (g/L) | NaHCO$_3$ (g/L) |
|---|---|---|---|
| Low bicarbonate concentrate | 90.73 | 2.06 | 28.35 |
| High bicarbonate concentrate | 82.84 | 2.06 | 39.70 |

TABLE 4b-continued

Compositions of the liquids concentrate

| Liquid | Na+ (mmol/L) | Mg2+ (mmol/L) | Cl- (mmol/L) | HCO3- (mmol/L) |
|---|---|---|---|---|
| Diluted Low bicarbonate concentrate | 140 | 0.75 | 116.5 | 25 |
| Diluted High bicarbonate concentrate | 140 | 0.75 | 106.5 | 35 |

TABLE 5b

Estimated osmotic pressures

| Composition Liquid | Osmotic Pressure (bar) (at 37° C.) |
|---|---|
| Low bicarbonate concentrate | 107.7 |
| High bicarbonate concentrate | 108.4 |
| Diluted Low bicarbonate concentrate | 7.5 |
| Diluted High bicarbonate concentrate | 7.7 |

The hemofiltrate drainage fluid will typically have an osmotic pressure on the same level as the diluted concentrate. Thus, as can be seen from table 5b, both concentrates provide useful positive osmotic potential differences relative to the hemofiltrate drainage in a forward osmotic process extracting water from a hemofiltrate drainage fluid.

Example 2. Preparation of Vesicles Containing Aquaporin Water Channels 1 mg/mL Asolectin proteoliposomes, and lipid to protein ratio (LPR) 200 using AqpZ Mw 27233 are prepared according to the following protocol:

1) Fill a 50 mL glass evaporation vial with 5 mL of a 2 mg/mL stock solution of asolectin (mW 786.11 g/mol, Sigma) in CHCl$_3$.
2) Evaporate the CHCl$_3$ using a rotation evaporator for at least 2 h to complete dryness.
3) Add 0.8 mL of buffer solution (1.3% octylglucoside (OG) in PBS pH 7.4) to rehydrate the film obtained in the evaporation vial in step 2.
4) Shake the vial at maximum rpm on a platform shaker (Heidolph orbital platform shaker Unimax 2010 or equivalent) until the lipid is dissolved.
5) Add 1.73 mg of AqpZ in a protein buffer containing Tris pH8, glucose and OG, 10 mg/mL, and rotate vial for 15 min at 200 rpm, the AqpZ being prepared according to description herein.

6) Slowly add 9.03 ml PBS (pH 7.4 without OG), and shake vial for 15 min at 200 rpm.
7) Freeze/thaw the combined solution/suspension on dry ice/40° C. water bath for three times to eliminate possible multilamellar structures.
8) Add 250 mg of hydrated Biobeads (SM2 from BioRad) and rotate vial for 1 h at 200 rpm at 4° C. to adsorb detergent (OG).
9) Add further 250 mg of hydrated Biobeads and rotate vial for 2 to 3 days at 200 rpm at 4° C.
10) The Biobeads with adsorbed OG are then removed by pipetting off the suspension.
11) Extrude the obtained suspension for about 11 times through a 200 nm polycarbonate filter using an extruder (such as an EmulsiFlex-05 from Avestin, Canada) at least 1 time and up to about 22 times to obtain a uniform proteoliposome suspension (vesicles) suspension.

Protocol for the Preparation of 1 mg/ml Proteo-Polymersomes Having a Polymer to Protein Ratio (POPR) of 50:

Polyoxazoline Based Triblock Copolymers, Poly(2-methyl oxazoline-b-dimethyl siloxane-b-2-methyl oxazoline, Moxa 12: DMS 35, Mw 3510) (P3691 purchased from Polymer Source™, Quebec, Canada), AqpZ Mw 27233

1) Fill a 50 ml glass evaporation vial with 5 ml of a 2 mg/ml stock solution of P3691 in $CHCl_3$.
2) Evaporate the $CHCl_3$ using a rotation evaporator for at least 2 h to complete dryness.
3) Add 3.0 mL of buffer solution (1.3% O.G.; 200 mM Sucrose; 10 mM Tris pH 8; 50 mM NaCl) to rehydrate the film obtained in the evaporation vial in step 2.
4) Shake the vial at 200 rpm on a platform shaker (Heidolph orbital platform shaker Unimax 2010 or equivalent) for 3 hours to obtain dissolution of the copolymer.
5) Add 1.55 mg µL of AqpZ in a protein buffer containing Tris, glucose and OG, and rotate vial over night at 200 rpm and 4° C.
6) Add 6.88 ml buffer (10 mM Tris pH 8; 50 mM NaCl) slowly while mixing up and down with pipette.
7) Add 180 mg hydrated Biobeads and rotate for 1 h at 200 rpm.
8) Add 210 mg hydrated Biobeads and rotate for 1 h at 200 rpm.
9) Add 240 mg hydrated Biobeads and rotate O.N. at 200 rpm 4° C.
10) Add 240 mg hydrated Biobeads and rotate O.N. at 200 rpm 4° C.
11) The Biobeads with adsorbed OG are then removed by pipetting off the suspension.
12) Extrude the suspension for about 21 times through a 200 nm polycarbonate filter using an extruder, such as from at least 1 time and up to about 22 times to obtain a uniform proteopolymersome suspension (vesicles) suspension.

Figure 1:
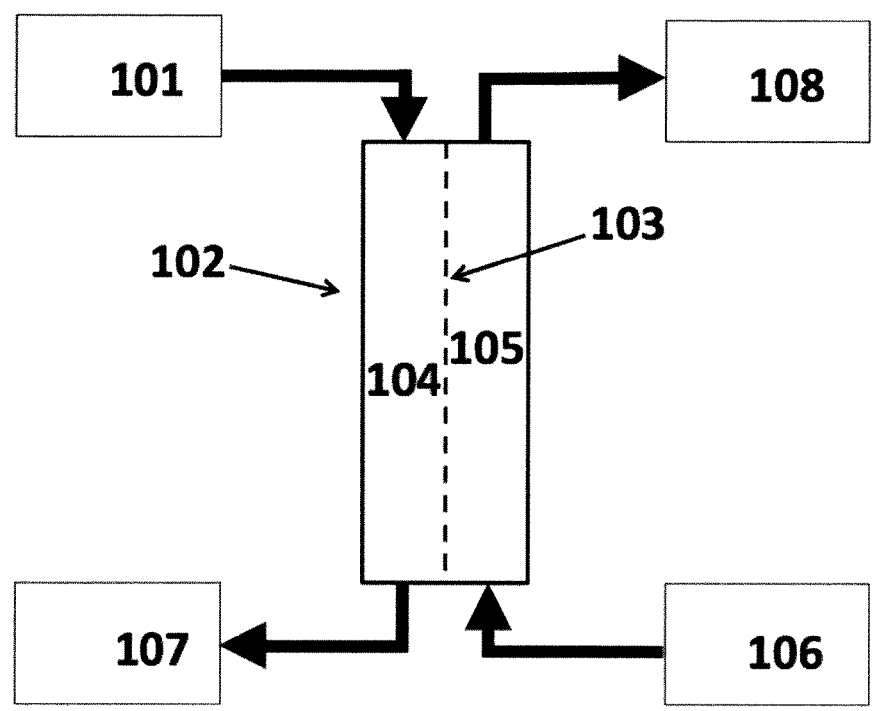
FIG. 1 shows a schematic diagram of a system according to the invention utilizing the water content of spent fluid from a renal replacement therapy process in which: (101) is the spent fluid; (102) is a forward osmosis (FO) unit; (103) is the forward osmosis (FO) membrane; (104) is the feed side; (105) is the draw side; (106) is a supply of dialysis or electrolyte replacement concentrate or a flow of blood having undergone hemofiltration; (107) is the dewatered spent fluid; (108) is the diluted concentrate or blood flow.

Example 3. Preparation of a Hollow Fiber Module Wherein the Inside Surface of the Fibres has been Functionalised with Immobilised AqpZ Vesicles Using a hollow fiber module having polyethersulfone membranes, such as a custom-made module, such as having 9 fibers corresponding to about 10 cm² outside area and 5 cm² inside area, or such as having a membrane area of up to 0.5 m² which may correspond to several hundred fibers depending on module length (Membrana GmbH, Wuppertal, Germany), the module being prepared essentially as described by Sukitpaneenit et al. 2011, a thin film composite layer is prepared on the inside fiber surface through interfacial polymerization involving the following steps:

1) Obtaining 4 mL of AqpZ vesicles in the form of proteoliposomes or proteopolymesomes as prepared in the example above.
2) Dissolve 250 mg of 1,3-diaminobenzene in 6 mL of MilliQ water to obtain a solution of 4.2% (w/w) concentration.
3) 75 mg of benzene-1,3,5-tricarbonyl chloride is dissolved in 50 mL of hexane to obtain a final concentration of 0.15% (w/v)
4) A 1,3-diaminobenzene/AqpZ vesicle mixture is prepared by dissolving/mixing 4 mL of the vesicles preparation from step 1 with 6 mL of the solution from step 2.
5) The mixture obtained in step 4 is constantly pumped through the module for 2 minutes using end inlet 1 (or inlet 2), cf. FIG. 1.
6) Excess 1,3-diaminobenzene is removed by a constant air purging of the lumen side of the fibers for 2 minutes using, e.g., inlet 1, cf. FIG. 1, preferably holding the module upside down.
7) A constant flow of the benzene-1,3,5-tricarbonyl chloride solution from step 3 is then injected into the module through inlet 1 for approximately 30 s using a syringe pump, e.g. from TSE systems (www.tse-systems.com), to allow the interfacial polymerization reaction to take place.
8) Finally, the module is preferably rinsed with MilliQ water, approximately 10 mL are used, by injection through side inlet 3 and 4.

After filling it with water the module is sealed with the white sealing caps (5), cf.

FIG. 1, to prevent it from drying out (the sealing caps are part of the module and it is delivered with them).

The forward osmosis module prepared according to the above protocol may be used in the method of the invention for reuse of pure water from spent dialysate solution. For more details about preparation of hollow fiber modules having thin film composite active fiber layers see WO 2014/108827, "A Hollow Fiber Module Having TFC-Aquaporin Modified Membranes" published on Jul. 17, 2014, the contents of which are incorporated herein by reference.

Example 4. A System for Utilizing Water from the Spent Dialysate from Hemodialysis This example shows the use of the system and method according to the invention for preparing a fresh dialysate for hemodialysis, cf. FIGS. 3A and 3B.

When starting the continuous preparation, the reservoir for the fresh and ready-to-use dialysate (301) holds a start volume of dialysate prepared beforehand. The fresh and ready-to-use dialysate (301) enters the dialyzer. After exit from the dialyzer the now spent dialysate (302) comprises ions (Na+, K+, lactate, acetate, bicarbonate, etc.), low molecular weight metabolites (e.g. urea) other metabolites (indoxyl, beta-2-microglobulin, etc.) and water. For utilizing water, the spent dialysate enters the first forward osmosis (FO) unit (307) on the feed side of the membrane. On the draw side of the membrane of this first FO unit runs the bicarbonate concentrate (305). During the FO process, the bicarbonate concentrate becomes diluted with water absorbed through the FO membrane from the spent dialysate.

Figure 3A:
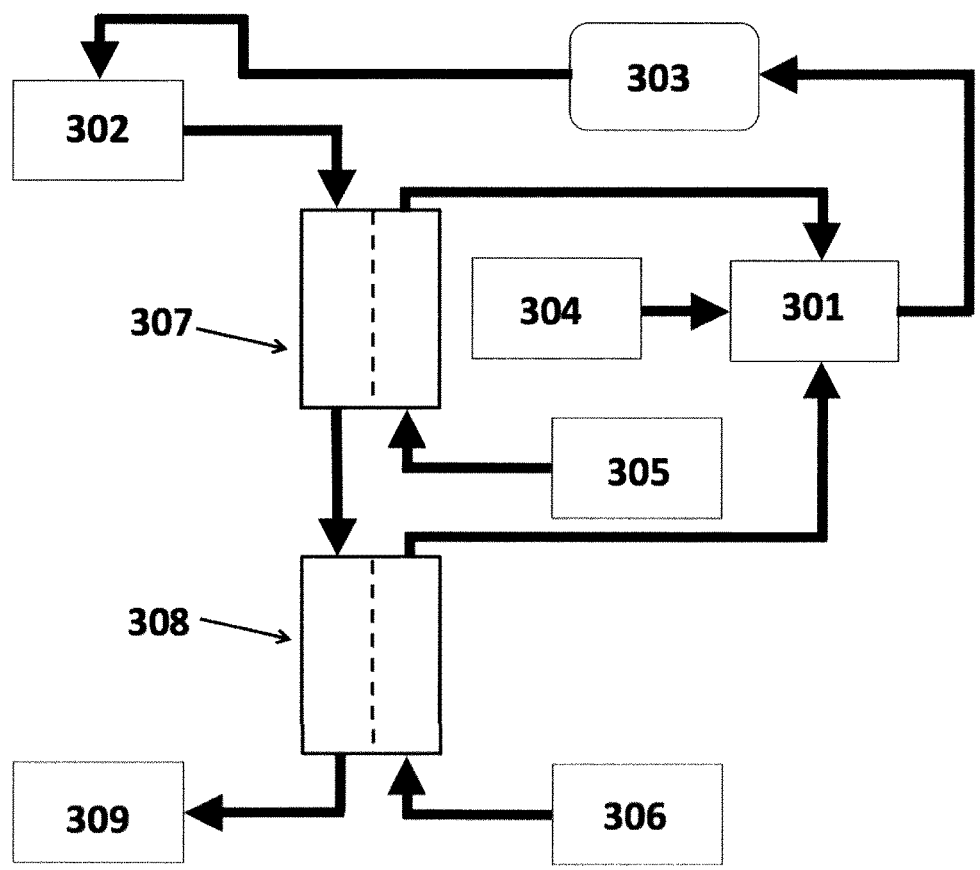
FIGS. 3A and 3B shows a schematic diagram of a system for preparing a fresh dialysate for hemodialysis based on two concentrates in which: (301) is the fresh dialysate; (302) is the spent dialysate; (303) is the dialyzer; (304) is a supply of purified water; (305) is the bicarbonate concentrate; (306) is the acid concentrate; (307) and (308) are FO units; and (309) is the dewatered spent dialysate. Cf. Example 4 below.

In the embodiment shown in FIG. 3A, after exit from the first FO unit, the spent dialysate enters the second forward osmosis unit (308) on the feed side of the membrane. On the draw side of the membrane of this second FO unit runs the acid concentrate (citrate, lactate, acetate) (306). During the FO process, the acid concentrate becomes diluted with water from the spent dialysate.

After exit from the second FO unit, the spent and dewatered dialysate (309) is discarded.

Figure 3B:
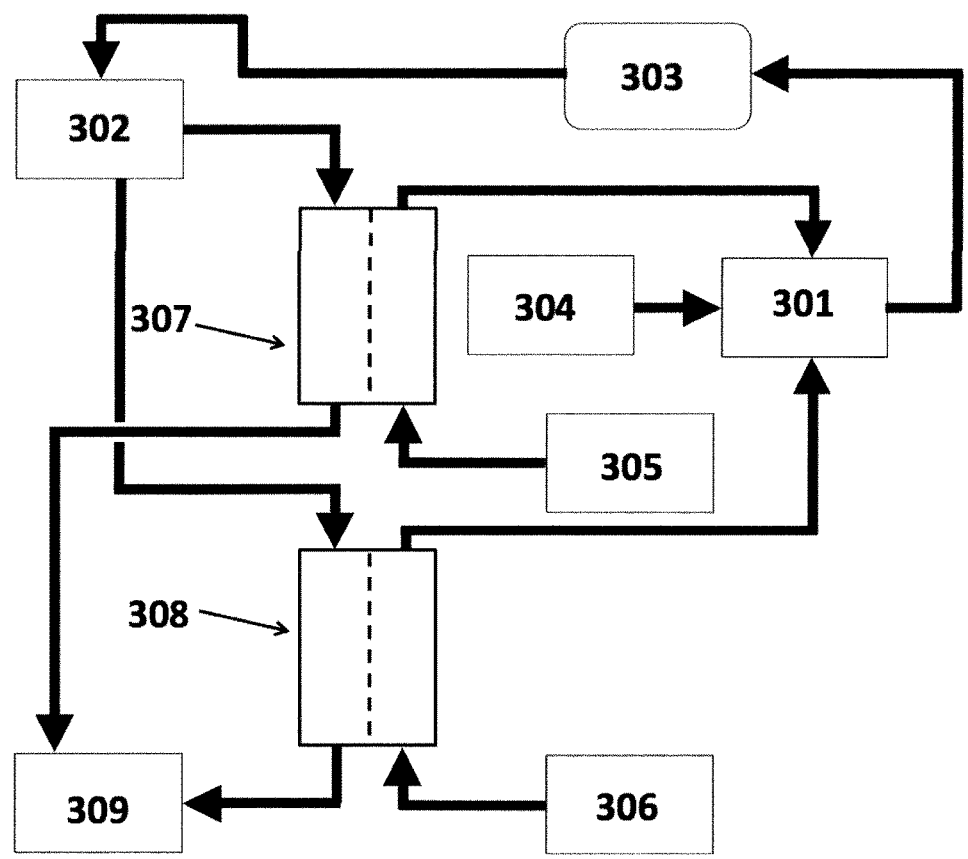

In the embodiment shown in FIG. 3B, after exit from the first FO unit, the spent and dewatered dialysate (309) is discarded. In parallel, the spent dialysate (302) enters the second forward osmosis unit (308) on the feed side of the membrane. On the draw side of the membrane of this second FO unit runs the acid concentrate (citrate, lactate, acetate) (306). During the FO process, the acid concentrate becomes diluted with water from the spent dialysate. After exit from the second FO unit, the spent and dewatered dialysate (309) is discarded.

The diluted bicarbonate concentrate and the diluted acid concentrate are mixed and adjusted as needed with purified water to obtain a fresh dialysate of the desired concentration of acidic and basic components.

Example 5. A Water Extraction System for Recycling of Hemodialysis Water from Spent Dialysis Solution This example shows the use of a highly water permeable FO membrane being essentially impermeable to salts and low molecular weight solutes in a water extraction process for post treatment of spent dialysate solutions, cf. FIG. 1. The dialysate solution is typically a diluted aqueous solution of mineral ions and glucose, which typically runs in a counter-current flow with blood from a patient through a hollow fiber ultrafiltration module during hemodialysis. Sam et al. (2006) discloses composition and clinical use of hemodialysates. The dialysate solution will maintain a sufficient concentration gradient across an ultrafiltration membrane with respect to the solutes that have to be removed from the blood, such as urea, degradation products such as indoxyl sulphate and p-cresol, and excess potassium and phosphorous, and thus maintain efficiency of the dialysis. For this purpose large quantities of ultrapure water are needed, i.a. about 400 L of water per week. The water extraction systems described herein are useful in systems for recycling of this ultrapure water, such as in a closed loop, where the (diluted) used or spent dialysate solution, after being used in hemodialysis, e.g. after absorbing waste materials such as urea and other metabolites from blood by passing through a hemodialysis filter may function as the source or feed solution (101) when passing through an FO membrane module, or flow cell (102) containing an aquaporin membrane prepared a disclosed herein, and where a concentrated fresh dialysate solution (dialysis concentrate) may function as the draw solution (106). In this way only pure water is extracted from the contaminated, waste dialysate solution (101) and this extracted pure water is used as a replacement for the otherwise required new supplements of ultrapure water for dilution of the dialysate concentrate (106). Ideally, the concentrated dialysate can be sufficiently diluted so as to be directly used for continued hemodialysis (108). Optionally, a supply of purified water may be used as a supplementary water source.

An additional advantage would result from the used dialysate solution becoming concentrated resulting in a smaller volume for waste disposal.

Figure 4:
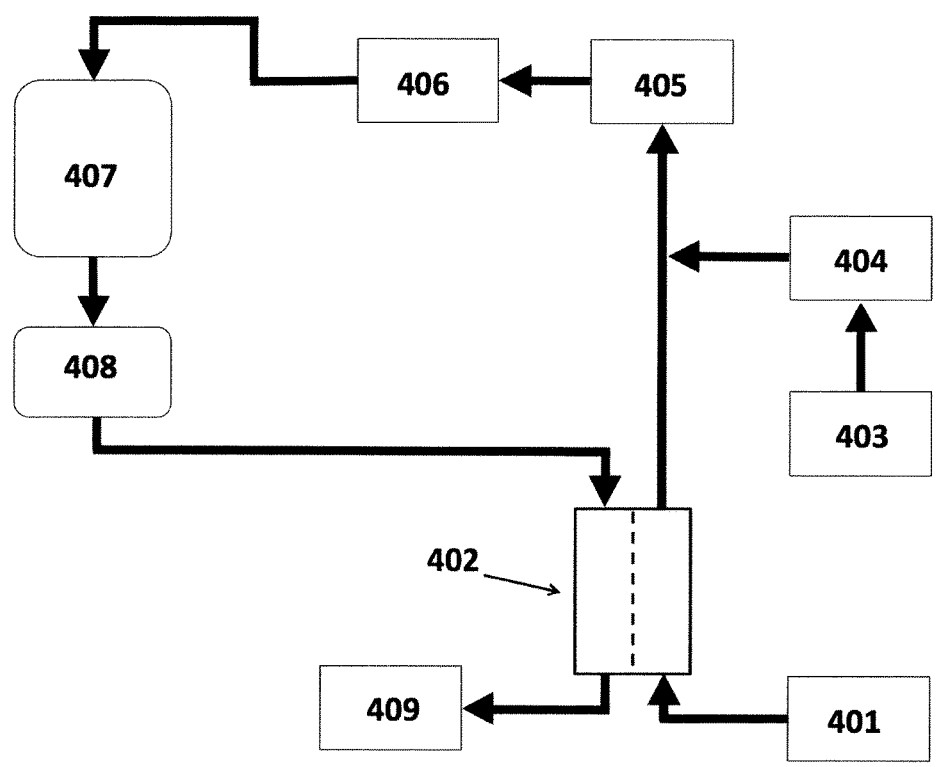
FIG. 4 shows a schematic diagram of a system for preparing a fresh dialysate for peritoneal dialysis in which: (401) is the acid concentrate; (402) is the FO unit; (403) is a supply of purified water; (404) is an ultrafiltration unit; (405) is a bicarbonate column; (406) is an ultrafiltration unit; (407) is a fresh dialysate reservoir; (408) is the patient and (409) is a container for dewatered spent dialysate. For more details refer to Example 6 below.

Example 6. A Water Extraction System for Re-Use of Water Lost Through Peritoneal Dialysis FIG. 4 shows a system for continuous preparation of peritoneal dialysis fluid where a forward osmosis unit is used to extract pure water from spent peritoneal dialysis fluid. This is an alternative to the use of multiple and high fill volume dialysate bags as used today and to using a supply of purified water from reverse osmosis and subsequent ultrafiltration, cf. Brunkhorst et al. (1998) who studied the feasibility of production of a dialysis fluid for peritoneal dialysis using a Gambro AK 100 Ultra machine which was developed for on-line production of intravenous substitution fluids for hemofiltration.

In the system according to the present invention the fresh dialysate for peritoneal dialysis is prepared from an acid concentrate (401) which flows through the draw side of the FO unit (402). On the feed side of the FO unit runs the spent dialysate from the patient (408). The diluted concentrate may optionally be further diluted from a supply of purified water (403), which water has undergone ultrafiltration in an ultrafiltration unit (404). The diluted concentrate then runs through a bicarbonate column (405) and then an ultrafiltration unit (406) before entering a reservoir for fresh dialysate (407). When starting the continuous preparation, the reservoir (407) holds a start volume of fresh dialysate prepared beforehand.

Re-using pure water obtained through FO extraction according to the invention herein adds additional benefits to the production of fresh dialysis fluids, because of elimination of the energy use necessary for the usual reverse osmosis and ultrafiltration processes in addition to other benefits, such as reduced dangers of toxic substance contamination etc.

Example 7. A Water Extraction System for Recycling of Water Lost Through Hemofiltration Here we describe how the system of the invention can be utilised in a hemofiltration setting for the preparation of replacement fluid for hemofiltration where the replacement fluid is similar in composition to a dialysate for hemodialysis except that it is isotonic.

Hemofiltration is a renal replacement therapy used in intensive care, such as for acute renal failure. It is a slow continuous therapy in which sessions usually last between 12 to 24 hours and are usually performed daily. During hemofiltration, a patient's blood is passed via a machine to a semipermeable membrane (the hemofilter), typically an ultrafiltration membrane, for removal of waste products and excess water.

To prevent hypovolemia (decrease in volume of blood plasma), water removed during hemofiltration must be added to the blood before it is returned to the patient. Hemofiltration rates such as 1 L/hr mean that one liter of fluid is removed from the patient's blood and eliminated in the drainage fluid and 1 L of replacement fluid is returned to the circuit before it reaches the patient.

The solute movement from the blood is governed by convection rather than by diffusion thus avoiding the use of the hypertonic dialysate. Instead, a positive hydrostatic pressure drives water and solutes across the hemofilter membrane from the blood compartment to the filtrate compartment, from which it is drained. Solutes pass through the membrane at a similar rate by the flow of water forced by the hydrostatic pressure. Thus convection overcomes the reduced removal rate of larger solutes due to their slow speed of diffusion, which is seen in hemodialysis. The isotonic replacement fluid is added to the blood to replace lost fluid volume and electrolytes in the drainage. The replacement fluid must be of high purity, because it is infused directly into the blood line of the extracorporeal circuit. Replacement fluids can be returned either pre or post hemofilter. This is referred to as predilution or post dilution sets. Predilution means that the replacement solution is returned to the blood before it reaches the filter, diluting the blood in the hollow fibers. Postdilution means that the replacement fluid is returned to the blood after the filter (but before the return side of the access catheter). Predilution dilutes the blood in the filter, reducing clotting. Postdilution concentrates the blood in the filter, enhancing clearance.

The system of the invention (referring to FIG. 5A) is useful in preparation of the replacement fluid by applying a relatively more concentrated solution (509) as the draw solution and applying the hemofiltrate drainage fluid (507) from the patient as the feed in a forward osmosis unit to obtain the proper isotonic replacement fluid using concentration adjustment measures as needed and passing through sterilization steps as needed. Optionally, a supply of isotonic replacement fluid (511) may be used as a supplementary water source. In the figure the replacement fluids is returned post hemofilter.

A commercial replacement fluid from Gambro, Hemosol B0, consists of a two compartment PVC bag containing an electrolyte solution in the small compartment (compartment A) and the buffer solution in the large compartment (compartment B).

Before reconstitution 1000 ml of electrolyte solution (small compartment A) contains: active substances: Calcium chloride, $2H_2O$ 5.145 g, magnesium chloride, $6H_2O$ 2.033 g, and lactic acid 5.400 g. 1000 ml of buffer solution (large compartment B) contains: active substances: Sodium hydrogen carbonate 3.090 g and sodium chloride 6.450 g.

After reconstitution the small and the large compartments are mixed to give one reconstituted solution whose ionic composition has a theoretical osmolarity of 287 mOsm/l:

| Substance | mmol/L | mEq/L |
|---|---|---|
| Calcium $Ca^{2+}$ | 1.75 | 3.50 |
| Magnesium $Mg^{2+}$ | 0.5 | 1.0 |
| Sodium $Na^+$ | 140 | 140 |
| Chloride $Cl^-$ | 109.5 | 109.5 |
| Lactate | 3 | 3 |
| Hydrogen carbonate $HCO_3^-$ | 32 | 32 |

Either of the electrolyte and the buffer concentrate will be useful in the form of a concentrate as a draw solution in combination with the drainage fluid as the feed. Through proper adjustment of osmotic gradient of the concentrate used as draw, and final addition of highly purified water for mixing into the final replacement fluid to obtain isotonicity, a considerable utilization of pure water from drainage fluid from the patient undergoing hemofiltration can be achieved.

For hemofiltration, one example of an electrolyte concentrate is the Normocarb HF™ series from Dialysis Solutions Inc: Undiluted Normocarb HF™ 25 contains 90.73 g/L sodium chloride, 2.06 g/L magnesium chloride hexahydrate and 28.35 g/L sodium bicarbonate in water for injection. Undiluted Normocarb HF™ 35 contains 82.84 g/L sodium chloride, 2.06 g/L magnesium chloride hexahydrate and 39.70 g/L sodium bicarbonate in water for injection. Both concentrates are to be diluted 13.5 times before use.

In a further embodiment, the filtrate, such as a microfiltrate or an ultrafiltrate, from hemofiltration can be shunted through a renal assist device (RAD) for re-extraction of water, cf. Issa et al. (2007), where said device is in the form of a hollow fiber unit having an active layer comprising aquaporin water channels, such as hollow fibres modified with a thin film composite layer comprising aquaporin water channels prepared as described above. Said device is shown as (506) in FIGS. 5B, 5C, and 5D. All of FIGS. 5A to 5D are adapted from Issa et al.

FIG. 5B shows a schematic hemofiltration setting for re-extraction of water from the filtrate (507) emanating from the hemofilter (502), which in this case is a HF module with the blood stream under hydrostatic pressure running inside the hollow microporous fibres. Subsequent to passage through the hemofilter the now concentrated blood runs through the extracapillary space or shellside of an HF module (506) co- or counter-current with the filtrate that runs in the lumen side of the hollow fibres under forward osmosis conditions or under pressure (by pumping) assisted forward osmosis. In this way postdilution replacement to the blood stream of water, ions and low molecular weight substances extracted to the concentrated blood from the relatively dilute filtrate feed takes place, providing that the module contains conventional nano- or microfilter fibres. In the case, however, where an HF module having aquaporin water channels immobilised in a thin film composite active layer prepared as described above is used, then the concentrated filtrated blood stream acting as a draw extracts only pure water from the hemofiltrate. Thus, salts, ions and low molecular solutes do diffuse across the hollow fibers and the patient may have to ingest salts as needed, or an isotonic saline may be infused intravenously if needed.

FIG. 5C shows a schematic hemofiltration setting comparable to FIG. 5A, but where a predilutional replacement fluid stream (512) enters the hemofilter.

FIG. 5D shows a schematic hemofiltration setting where a postdilutional replacement fluid stream (513) enters the filtered blood steam directly following re-extraction of water from the hemofiltrate.

An example of a commercial hemofiltration unit is Prismaflex M150 Set from Gambro having an active filter area of 1.5 $m^2$. The hollow fiber internal diameter (wet) is 240 µm, and fiber wall thickness is 50 µm.

Another example is Nipro's hollow fiber hemofilter UF-205, wherein the inner fibre membrane is made from triacetate, with a diameter of 200 µm and a thickness of 15 µm. The outer casing is made from polycarbonate and polyurethane, sterilized with gamma radiation. The unit is designed to withstand pressures up to 500 mmHg, For hollow fiber hemofiltration units high molecular composite membrane polysulfone fibers may be used having a pore diameter of 0.005 µm-0.05 µm. These and similar hollow fibers may be used in FO modules for reabsorption of water from filtrates or spent fluids from renal replacement therapy processes, and said fibers may be modified with a thin film composite membrane having incorporated aquaporin water channels for enhanced water flux and selectivity.

Figure 5E:
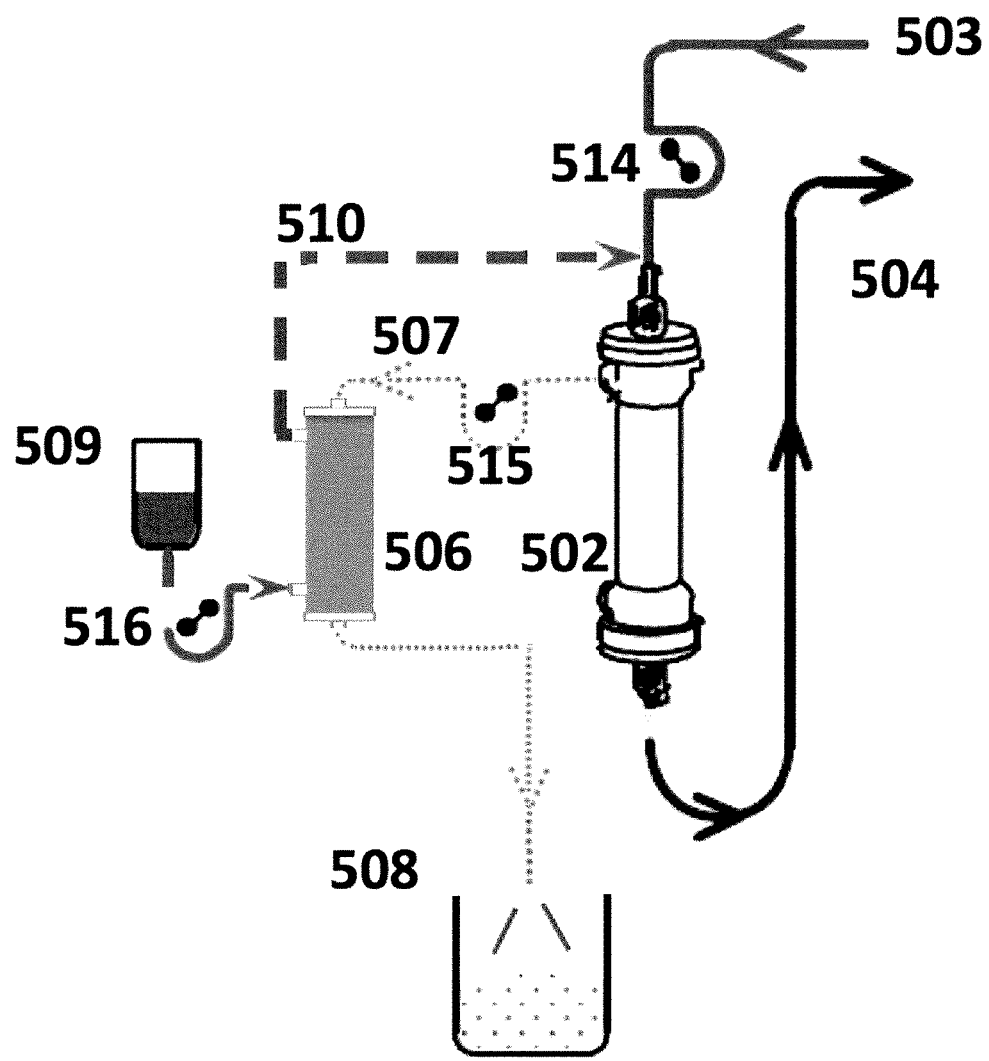

FIG. 5E shows how a system similar to the system from FIG. 5A works with pumps (514, 515, 516) for pumping the blood to the hemofilter (pump 514), the filtrate through the forward osmosis (FO) module (pump 515) and the electrolyte-containing replacement concentrate through the FO module (pump 516). The system of FIG. 5E works with predilution of the blood. The pump (516) may also yield a hydraulic pressure to provide an assisted forward osmosis in the module (506).

Example 8. FO Proof-of-Concept Study

Figure 7:
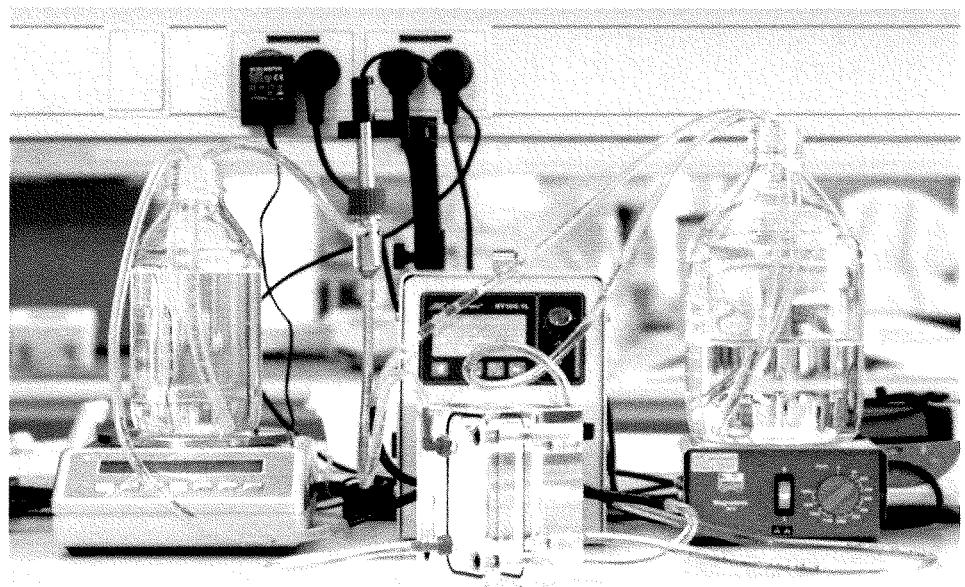
FIG. 7 shows a bench-scale forward osmosis experiment set-up. For more details refer to Example 8 and 9.

In this example we provide a protocol for a forward osmosis water extraction study for preparation of a ready-to-use dialysate using both an acidic and a basic dialysate concentrate as the draw solution and an artificially prepared spent dialysate solution as the feed solution. Here we describe two FO membrane setup cycles simulating the water extraction systems described in Example 4 (with reference numbers from FIG. 3B and with reference to FIG. 7 showing a typical bench top setting for forward osmosis). Cycle 1: feed (302), chamber (307), up concentrated feed (309), draw (305), the FO chamber (307) and the diluted draw (301).

Test Solutions:

The feed solution is an artificially prepared spent dialysate solution (302) containing: urea, creatinine, o-cresol, p-cresol, indoxyl acetate/sulfate and beta-microglobulin. It is made up to a concentration resulting in a typical concentration found in blood to result in 0.3 Osmol/L. The osmolality of the feed solution is measured by Osmomat 030, Gonotec GmbH.

The concentrated basic draw solution (305) is a 1 mol/L bicarbonate solution. It is made up to an osmolality of 1.7 Osmol/L corresponding to an osmotic pressure of 40 bars. The FO Chamber (307):

The FO experiments are performed with a bench-scale membrane system consisting of a CF042 Cell (Sterlitech, Kent, Wash.) as the cross flow membrane filtration unit. FIG. 7 The FO membrane (for example an Aquaporin Inside™ FO membrane (42 cm$^2$) is placed with the active side facing the feed.

A 500 mL feed solution reservoir and a 500 mL stirred draw solution reservoir are connected to the membrane cell. The solutions are pumped in counter-current flow at 50 mL/min with one peristaltic pump (BT100-1 L, Longer Pump, China).

The feed reservoir is placed on a digital scale (Kern 572, Kern & Sohn GmbH, Germany) and a conductivity probe is installed in the feed circuit (Orion 3 star meter—013016MD probe, Thermo Scientific, Waltham, Mass.).

A computer monitors the measurements to calculate an online water flux and reverse salt flux. Manual samples are taken from the draw solution to measure the rejection of the organic compounds from the feed solution, which are being determined by common analytical tools/methods like HPLC after solid phase extraction. Previous unpublished test results have shown a >95-99% rejection of creatinine in a similar FO setup, but with the use of a hollow fiber Aquaporin Inside™ FO module.

Cycle 2: feed (302), chamber (308), up concentrated feed (309), draw (306), the FO chamber (308) and the diluted draw (301).

Test Solutions:

The feed solution is an artificially prepared spent dialysate solution described above.

The draw solution (306) is an acid concentrate, e.g. made up according to the compounds and concentrations given in table 4.

FO Chamber (308):

The connection of the feed, draw and the monitoring of the experiment is performed similar to the set-up in chamber (307).

Finally, the acid and the base dialysate solutions having been diluted with pure water extracted from the feed during the FO processes are combined and a purified water source is used to adjust the osmolality to the needed hypertonicity for use in a hemodialysis setting. Analysis of samples from each of the two diluted draw solutions are expected to prove very high rejections of the analytes, e.g.: urea, creatinine, o-cresol, p-cresol, indoxyl acetate/sulfate and beta-microglobulin.

Example 9. FO Proof-of-Concept Study

In this example we provide a protocol for a forward osmosis water extraction study for preparation of a ready-to-use replacement fluid using a replacement fluid concentrate as the draw solution and a hemofiltrate drainage fluid (effluent) as the feed solution. Here we describe an FO membrane setup cycle simulating the water extraction systems described in Example 7 (with reference numbers from FIG. 5A and with reference to FIG. 7 showing a typical bench top setting for forward osmosis).

Cycle: feed (hemofiltrate drainage fluid) (507), up concentrated feed (508), draw (concentrated replacement fluid) (509), the FO chamber (506) and the diluted draw (510).

Test Solutions:

The feed solution is an hemofiltrate drainage fluid (507) obtained from an intensive care unit. The osmolality of the feed solution is measured by Osmomat 030, Gonotec GmbH.

The concentrated replacement fluid (509) is a solution containing 90.73 g/L sodium chloride, 2.06 g/L magnesium chloride hexahydrate and 28.35 g/L sodium bicarbonate. It corresponds to an osmotic pressure of about 108 bar, cf. Example 1b.

The FO Chamber (506):

The FO experiments are performed with a bench-scale membrane system consisting of a CF042 Cell (Sterlitech, Kent, Wash.) as the cross flow membrane filtration unit. FIG. 7 The FO membrane (for example an Aquaporin Inside™ FO membrane (42 cm$^2$) is placed with the active side facing the feed.

A 500 mL feed solution reservoir and a 500 mL stirred draw solution reservoir are connected to the membrane cell. The solutions are pumped in counter-current flow at 50 mL/min with one peristaltic pump (BT100-1 L, Longer Pump, China).

The feed reservoir is placed on a digital scale (Kern 572, Kern & Sohn GmbH, Germany) and a conductivity probe is installed in the feed circuit (Orion 3 star meter—013016MD probe, Thermo Scientific, Waltham, Mass.).

A computer monitors the measurements to calculate an online water flux and reverse salt flux. Manual samples are taken from the draw solution to measure the rejection of the organic compounds from the feed solution, which are being determined by common analytical tools/methods like HPLC after solid phase extraction.

Alternatively, a set-up with an Aquaporin Inside™ hollow fiber FO module can be used.

REFERENCES

All documents mentioned in this specification are incorporated herein by reference in their entirety.

Panu Sukitpaneenit and Tai-Shung Chung, Environmental Science & Technology, 2012, 46, 7358-7365

Brunkhorst et al., Nephrol Dial Transplant (1998) 13: 3189-3192, Automated peritoneal dialysis with 'on-line'-prepared bicarbonate-buffered dialysate: technique and first clinical experiences Discher, B. M., Hammer, D. A., Bates F. S., Discher D. E., Polymer Vesicles in Various Media, Current Opinion in Colloid & Interface Science 5 (2000)125-131

Discher D. E., et al., Polymer Vesicles, Science 297, 967 (2002)

Sam R., Vaseemuddin M., Leong W. H., Rogers B. E., Kjellstrand C. M., Ing T. S., Composition and clinical use of hemodialysates, Hemodialysis International 2006; 10: 15-28

Harris J. K., Gene D. Rose, and Merlin L. Bruening, Spontaneous Generation of Multilamellar Vesicles from Ethylene Oxide/Butylene Oxide Diblock Copolymers, Langmuir 2002, 18, 5337-5342

Nardin C., Thomas Hirt, Jörg Leukel, and Wolfgang Meier, Polymerized ABA Triblock Copolymer Vesicles, Langmuir 2000, 16, 1035-1041

Alsvik and Hägg, Pressure Retarded Osmosis and Forward Osmosis Membranes: Materials and Methods; Polymers 2013, 5, 303-327.

Naim Issa, Jennifer Messer, Emil P. Paganini, Renal Assist Device and Treatment of Sepsis-Induced Acute Kidney Injury in Intensive Care Units, in Ronco C, Bellomo R, Kellum JA (eds): Acute Kidney Injury. Contrib Nephrol. Basel, Karger, 2007, vol 156, pp 419-427.

WO 2014/075086: Methods for reducing ion exchange and reverse salt flux phenomena in membranes for osmotically driven membrane processes (Nagare Membranes LLC).

US 2010/0121246 A1

Ronco, C. (2006) Critical Care 10:123 (doi:10.1186/cc4843)

The invention claimed is:

1. A system for recycling at least a part of the water content in waste fluid from a hemofiltration process resulting in a flux of water from said waste fluid into a supply of electrolyte replacement concentrate or into a stream of concentrated blood resulting from said hemofiltration, said system comprising a forward osmosis (FO) unit comprising a forward osmosis membrane comprising nanoporous water channels, said membrane having a feed side and a draw side wherein the feed side is in fluid communication with said waste fluid being the filtrate from a patient undergoing said hemofiltration, and wherein the draw side is in fluid communication with a supply of said electrolyte concentrate or wherein the draw side is in fluid communication with a stream of concentrated blood resulting from said hemofiltration.

2. The system according to claim 1, wherein said system further comprises pumps for said feed and said draw fluids.

3. The system according to claim 1, wherein said nanoporous water channels are selected from the group consisting of nanoparticles, nanotubes, carbon nanotubes, graphene based materials, aquaporin water channels and biomimetic synthetic water selective porous material.

4. The system according to claim 1, wherein said nanoporous water channels are aquaporin water channels.

5. The system according to claim 4, wherein the membrane comprises:
an active layer comprising immobilized aquaporin water channels, and
a support layer.

6. The system according to claim 5, wherein said active layer is a cross linked aromatic amide layer, preferably formed by interfacial polymerization, wherein aquaporin vesicles are incorporated, said vesicles being formed by self assembly of amphiphilic matrix forming compounds in the presence of an aquaporin protein preparation.

7. The system according to claim 6, wherein said amphiphilic matrix forming compounds are selected from an amphiphilic lipid, a hydrophobin, a diblock copolymer, a triblock copolymer or mixtures thereof.

8. The system according to claim 5, wherein said active layer comprises a thin film composite (TFC) membrane.

9. The system according to claim 4, wherein said aquaporin water channel is selected from the group consisting of aquaporins of procaryotic origin, mammalian aquaporins, plant aquaporins, yeast aquaporins, and aquaglyceroporins.

10. The system according to claim 1, further comprising means for pressurizing said feed resulting in a pressure assisted forward osmosis process.

11. A hemofiltration machine comprising the system for utilizing the spent fluid from a renal replacement therapy process according to claim 1.

12. A method for recycling at least a part of the water content in waste fluid from a hemofiltration process resulting in a flux of water from said waste fluid into a supply of electrolyte replacement concentrate or into a stream of concentrated blood resulting from said hemofiltration, the method comprising
providing a system comprising a forward osmosis (FO) unit comprising a forward osmosis membrane comprising nanoporous water channels, said membrane having a feed side and a draw side wherein the feed side is in fluid communication with said waste fluid being the filtrate from a patient undergoing said hemofiltration, and wherein the draw side is in fluid communication with a supply of said electrolyte concentrate or wherein the draw side is in fluid communication with a stream of concentrated blood resulting from said hemofiltration;
supplying to the system the waste fluid from a patient undergoing said hemofiltration to a feed side of a forward osmosis (FO) unit comprising a forward osmosis membrane comprising nanoporous water channels;
extracting filtrate from a draw side of the membrane of the forward osmosis (FO) unit, wherein the draw side is in fluid communication with a supply of said electrolyte concentrate or wherein the draw side is in fluid communication with a stream of concentrated blood resulting from said hemofiltration, thereby recycling at least a part of the water content in the waste fluid from the hemofiltration process.

13. A forward osmosis membrane comprising nanoporous water channels for use in a method of treating a patient undergoing a hemofiltration in the course of renal replacement therapy, wherein the membrane is part of a forward osmosis (FO) unit and has a feed side and a draw side, the feed side being in fluid communication with a waste fluid which is a filtrate from the patient and the draw side being in fluid communication with a supply of said electrolyte concentrate or a stream of concentrated blood resulting from the hemofiltration, so that a part of the water content in the waste fluid from the hemofiltration is recycled, resulting in a flux of water from the waste fluid into a supply of electrolyte replacement concentrate or into a stream of concentrated blood resulting from said hemofiltration.

14. The forward osmosis membrane according to claim 13, wherein said nanoporous water channels are selected from the group consisting of nanoparticles, nanotubes, carbon nanotubes, graphene based materials, aquaporin water channels and biomimetic synthetic water selective porous material.

15. The forward osmosis membrane according to claim 13, wherein said nanoporous water channels are aquaporin water channels.

16. The forward osmosis membrane according to claim 15, wherein the membrane comprises:
an active layer comprising immobilized aquaporin water channels, and
a support layer.

17. The forward osmosis membrane according to claim 16, wherein said active layer is a cross linked aromatic amide layer, preferably formed by interfacial polymerization, wherein aquaporin vesicles are incorporated, said vesicles being formed by self assembly of amphiphilic matrix forming compounds in the presence of an aquaporin protein preparation.

18. The forward osmosis membrane according to claim 17, wherein said amphiphilic matrix forming compounds are selected from the group consisting of an amphiphilic lipid, a hydrophobin, a diblock copolymer, a triblock copolymer and mixtures thereof.

19. The forward osmosis membrane according to claim 13, wherein the membrane is a thin film composite (TFC) membrane.

20. The forward osmosis membrane according to claim 13, wherein said aquaporin water channel is selected from the group consisting of aquaporins of procaryotic origin, mammalian aquaporins, plant aquaporins, yeast aquaporins, and aquaglyceroporins.

21. An artificial kidney apparatus comprising
a) an ultrafiltration unit for the removal of solutes from blood plasma from a patient needing such treatment resulting in a stream of diluted filtrate from said plasma and a stream of concentrated blood having lost water and solutes through the ultrafiltration; said apparatus further comprising
b) a forward osmosis unit having an aquaporin containing membrane having a feed side and a draw side, the membrane being substantially impenetrable to solutes and essentially allowing only water to permeate, wherein the filtrate from said ultrafiltration unit is in fluid communication with the feed side and the concentrated blood is in fluid communication with the draw side resulting in a reuptake of water, but not solutes, from the filtrate to the blood allowing the blood to be reintroduced to the patients blood stream and the simultaneously volume reduced filtrate to be discarded, and
c) means for pumping the streams of blood and filtrates as needed in said apparatus.

22. The artificial kidney apparatus of claim 21 having an additional stream of replacement fluid fitted either in predilution mode or in postdilution mode relative to the ultrafiltration unit or forward osmosis unit.

23. The system according to claim 9, wherein said aquaporin water channel is:
(i) an aquaporin of procaryotic origin, wherein the aquaporin of procaryotic origin is AqpZ;
(ii) a mammalian aquaporin, wherein the mammalian aquaporin is Aqp1 and Aqp2;
(iii) a plant aquaporin, wherein the plant aquaporin is a plasma intrinsic protein (PIP), a tonoplast intrinsic protein (TIP), a nodulin intrinsic protein (NIP), or a small intrinsic proteins (SIP)
(iv) a yeast aquaporin, wherein the yeast aquaporin is AQY1 or AQY2; or
(v) an aquaglyceroporin, wherein the aquaglyceroporin is GlpF or Yfl054.

24. The system according to claim 23, wherein the SIP is SoPIP2; 1, PttPIP2; 5, or PtPIP2; 2.

25. The forward osmosis membrane according to claim 20, wherein said aquaporin water channel is:
(i) an aquaporin of procaryotic origin, wherein the aquaporin of procaryotic origin is AqpZ;
(ii) a mammalian aquaporin, wherein the mammalian aquaporin is Aqp1 and Aqp2;
(iii) a plant aquaporin, wherein the plant aquaporin is a plasma intrinsic protein (PIP), a tonoplast intrinsic protein (TIP), a nodulin intrinsic protein (NIP), or a small intrinsic proteins (SIP)
(iv) a yeast aquaporin, wherein the yeast aquaporin is AQY1 or AQY2; or
(v) an aquaglyceroporin, wherein the aquaglyceroporin is GlpF or Yfl054.

26. The forward osmosis membrane according to claim 25, wherein the SIP is SoPIP2; 1, PttPIP2; 5, or PtPIP2; 2.

* * * * *